United States Patent
Huang et al.

(10) Patent No.: US 7,112,337 B2
(45) Date of Patent: Sep. 26, 2006

(54) LIPOSOME COMPOSITION FOR DELIVERY OF NUCLEIC ACID

(75) Inventors: Shi-Kun Huang, Castro Valley, CA (US); Samuel Zalipsky, Redwood City, CA (US); Wei-Ming Zhang, San Francisco, CA (US)

(73) Assignee: ALZA Corporation, Mountain View, CA (US)

( * ) Notice: Subject to any disclaimer, the term of this patent is extended or adjusted under 35 U.S.C. 154(b) by 734 days.

(21) Appl. No.: 10/020,671

(22) Filed: Dec. 12, 2001

(65) Prior Publication Data

US 2003/0031704 A1 Feb. 13, 2003

Related U.S. Application Data

(63) Continuation-in-part of application No. 09/685,940, filed on Oct. 10, 2000, and a continuation-in-part of application No. 09/556,056, filed on Apr. 21, 2000, now Pat. No. 6,342,244

(60) Provisional application No. 60/158,693, filed on Oct. 8, 1999, and provisional application No. 60/130,897, filed on Apr. 23, 1999, now abandoned.

(51) Int. Cl.
*A61K 9/127* (2006.01)

(52) U.S. Cl. .......................... 424/450; 514/44
(58) Field of Classification Search ............... 424/450, 424/1.21, 9.321, 9.51, 417; 428/402.2; 514/44
See application file for complete search history.

(56) References Cited

U.S. PATENT DOCUMENTS

| | | | |
|---|---|---|---|
| 4,179,337 A | 12/1979 | Davis et al. | |
| 4,766,106 A | 8/1988 | Katre et al. | |
| 4,902,502 A | 2/1990 | Nitecki et al. | |
| 4,917,888 A | 4/1990 | Katre et al. | |
| 4,935,465 A | 6/1990 | Garman | |
| 5,013,556 A | 5/1991 | Woodle et al. | |
| 5,103,556 A | 4/1992 | Filip et al. | |
| 5,395,619 A | 3/1995 | Zalipsky et al. | |
| 5,631,018 A | 5/1997 | Zalipsky et al. | |
| 5,851,818 A | 12/1998 | Huang et al. | |
| 5,965,434 A * | 10/1999 | Wolff et al. .............. | 435/320.1 |
| 6,180,134 B1 | 1/2001 | Zalipsky et al. | |
| 6,342,244 B1 | 1/2002 | Zalipsky | |
| 6,365,179 B1 | 4/2002 | Zalipsky et al. | |

FOREIGN PATENT DOCUMENTS

| | | |
|---|---|---|
| EP | 0 317 957 A2 | 5/1989 |
| WO | WO 97/07784 A2 | 3/1997 |
| WO | WO 98/16201 | 4/1998 |

OTHER PUBLICATIONS

Zalipsky, et al., "Peptides: The Wave of the Future", *Proceedings of the Second International and the Seventeenth American Peptide Symposium*, San Diego, Jun. 9–14, pp. 953–954, (2001).

Allen, T.M., et al., *Biochemica et Biophysica Acta* pp. 99–108, (1995).

Brois, S.J., et al., *J. Amer. Chem. Soc.* 92(26):7629–7631, (1970).

(Continued)

*Primary Examiner*—Gollamudi S. Kishore
(74) *Attorney, Agent, or Firm*—Perkins Coie LLP

(57) ABSTRACT

A liposome composition for delivery of a nucleic acid in vivo or ex vivo is described. The liposomes in the composition are comprised of (i) a lipid that is neutral in charge at physiologic pH and positively charged at pH values less than physiologic pH and (ii) a lipid joined to a hydrophilic polymer by a dithiobenzyl linkage. The liposomes are associated with a nucleic acid for delivery to a cell.

26 Claims, 11 Drawing Sheets

OTHER PUBLICATIONS

Conner, et al., *Proc Natl. Acad Sci USA*, p. 1715, (1984).
Chu and Szoka, *J. Liposome Res* 4(1):361, (1994).
Dittmer, J.C., et al., *J. Lipid Res.* pp. 126–127, (1964).
Grice, R., et al., *J. Chem. Soc.* pp. 1947–1954, (1963).
Kaneko, T., et al., *Bioconjugate Chem.* 2(3):133–141, (1991).
Kirpotin, D., et al., *FEBS Letters* 388:115–118, (1996).
Lasic, D., and Martin, F., Stealth Liposomes, Chapter 9, pp. 93–102, CRC Press, Boca Raton, Fl., (1995).
Lash, L.H., et al., *Arch. Biochem. Biophys.* 240(2):583–592, (1985).
Martin, F.J., *Specialized Drug Del Systems–Manuf & Prod Tech* pp. 267–316, (1990).
Müeller, C.E., et al., *Arch Pyharm* 322(6):343–350, (1989).
Szoka, et al., *Ann Rev Biophys Bioeng*, p. 467, (1980).
Senter, P.D., et al., *J Org Chem* 55(9):2975–2978, (1990).
Veronese, et al., *Applied Biochem and Biotech*, pp. 141–152, (1985).
Zalipsky, et al., *Biotechnol Appl Biochem*, pp. 100–114, (1992).
Zalipsky, et al., *Eur Polymer J* 19(12):1177–1183, (1983).
Zalipsky, et al., *Bioconj Chem* 4(4):296–299, (1993).
Zalipsky, et al., *FEBS Lett* 353:71–74, (1994).
Zalipsky, et al., *Bioconjugate Chem* 6(6):705–708, (1995).
Zalipsky, *Bioconj Chem* 10(5):703–707, (1999).
Xu & Szoka, *Biochemistry*, pp. 5616–5623, (1996).
Felgner, P. et al., "Lipofection: A highly efficient, lipid-mediated DNA-transfection procedure", *Proc. Natl. Acad. Sci. USA* 84:7413–7417, 1987.
Morishita, R., et al., "Novel and Effective Gene Transfer Technique for Study of Vascular Renin Angiotensin System", *J. Clin. Invest.* 91:2580–2585, 1993.
Mulligan, R., "The Basic Science of Gene Therapy", *Science* 260:926–932, 1993.
Gabizon, A. et al., "Targeting Folate Receptor with Folate Linked to Extremities of Poly(ethylene glycol)–Grafted Liposomes: In Vitro Studies", *Bioconjugate Chem.* 10:289–298, 1999.

* cited by examiner

LIPOSOME COMPOSITION FOR DELIVERY OF NUCLEIC ACID

This application is a continuation-in-part of U.S. application Ser. No. 09/556,056 filed Apr. 21, 2000, now U.S. Pat. No. 6,342,244, which claims the priority of U.S. Provisional Application No. 60/130,897 filed Apr. 23, 1999, now abandoned; and this application is a continuation-in-part of U.S. application Ser. No. 09/685,940 filed Oct. 10, 2000, now pending, which claims the priority of U.S. Provisional Application No. 60/158,693, filed Oct. 8, 1999. Each of these applications are incorporated herein by reference in their entirety.

FIELD OF THE INVENTION

The present invention relates to liposome compositions for delivery of nucleic acids. More particularly, the invention relates to a liposome composition that includes a pH-responsive lipid and a surface coating of releasable hydrophilic polymer chains for administration of nucleic acids.

BACKGROUND OF THE INVENTION

A variety of methods have been developed to facilitate the transfer of genetic material into specific cells. These methods are useful for both in vivo or ex vivo gene transfer. In the former, a gene is directly introduced (intravenously, intraperitoneally, aerosol, etc.) into a subject. In ex vivo (or in vitro) gene transfer, the gene is introduced into cells after removal of the cells from specific tissue of an individual. The transfected cells are then introduced back into the subject.

Delivery systems for achieving in vivo and ex vivo gene therapy include viral vectors, such as retroviral vectors or adenovirus vectors, microinjection, electroporation, protoplast fusion, calcium phosphate, and liposomes (Felgner, J., et al., *Proc. Natl. Acad. Sci. USA* 84:7413–7417 (1987); Mulligan, R. S., *Science* 260:926–932 (1993); Morishita, R., et al., *J. Clin. Invest.* 91:2580–2585 (1993)).

Delivery of genetic material to cells using liposomal carriers has been widely studied. It is generally understood that liposome vesicles are taken up by cells via endocytosis and enter the lysosomal degradation pathway. Thus, some effort towards designing liposomes that avoid degradation has been made.

The use of cationic lipids, e.g., derivatives of glycolipids with a positively charged ammonium or sulfonium ion-containing headgroup, for delivery of negatively-charged biomolecules, such as oligonucleotides and DNA fragments, as a liposome lipid bilayer component is widely reported. The positively-charged headgroup of the lipid interacts with the negatively-charged cell surface, facilitating contact and delivery of the biomolecule to the cell. The positive charge of the cationic lipid is further important for nucleic acid complexation.

However, systemic administration of such cationic liposome/nucleic acid complexes leads to their facile entrapment in the lung. This lung localization is caused by the strong positive surface charge of the conventional cationic complexes. In vivo gene expression of the conventional cationic complexes with reporter gene has been documented in the lung, heart, liver, kidney, and spleen following intravenous administration. However, morphological examination indicates that the majority of the expression is in endothelial cells lining the blood vessels in the lung. A potential explanation for this observation is that the lung is the first organ that cationic liposome/nucleic acid complexes encounter after intravenous injection. Additionally, there is a large surface area of endothelial cells in the lung, which provides a readily accessible target for the cationic liposome/nucleic acid complexes.

Although early results were encouraging, intravenous injection of simple cationic liposomes has not proved useful for the delivery of genes to systemic sites of disease (such as solid tumors other than lung tumors) or to the desired sites for clinically relevant gene expression (such as p53 or HSV-tk) Cationic liposomes are cleared too rapidly, and present a host of safety concerns.

Another approach has been to include in the liposome a pH sensitive lipid, such as palmitoylhomocysteine (Connor, J., et al., *Proc. Natl. Acad. Sci. USA* 81:1715 (1984); Chu, C.-J. and Szoka, F., *J. Liposome Res.* 4(1):361 (1994)). Such pH sensitive lipids at neutral pH are negatively charged and are stably incorporated into the liposome lipid bilayers. However, at weakly acidic pH (pH<6.8) the lipid becomes neutral in charge and changes in structure sufficiently to destabilize the liposome bilayers. The lipid when incorporated into a liposome that has been taken into an endosome, where the pH is reported to be between 5.0–6.0, destabilizes and causes a release of the liposome contents.

In addition, tumor cell direct targeting is much more challenging than angiogenic endothelial cell targeting. Liposome/DNA complexes access angiogenic endothelial cells of tumor vasculature relatively easily, since the cells are directly exposed in the blood compartment. For targeting of tumor cells, liposome/DNA complexes need to extravasate through the leaky tumor blood vessels and then can reach tumor cells. Thus the complex stability, size, surface charge, blood circulation time, and transfection efficiency of complexes are all factors for tumor cell transfection and expression.

SUMMARY OF THE INVENTION

Accordingly, it is an object of the invention to provide a composition for systemic delivery of nucleic acid to a cell.

It is another object of the invention to provide a liposome comprising a neutral cationic lipid, a lipid derivatized with a releasable hydrophilic polymer. The liposome is associated with a nucleic acid for subsequent delivery of the nucleic acid to a cell or tissue.

Accordingly, in one aspect, the invention includes a composition for administration of a nucleic acid, comprising (a) liposomes comprised of (i) a lipid having the formula:

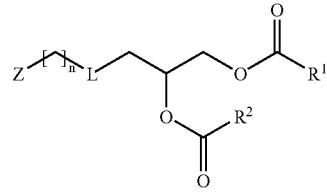

where each of $R^1$ and $R^2$ is an alkyl or alkenyl chain having between 8–24 carbon atoms, and each of $R^1$ and $R^2$ are independently selected; n=0–20; L is selected from the group consisting of (1) —X—(C=O)—Y—[[CH$_2$—]], (2) —X—(C=O)—, and (3) —X—[[CH$_2$—]], where X and Y are independently selected from oxygen, NH and a direct bond; Z is a weakly basic moiety that has a pK of less than 7.4 and greater than about 4.0.

The liposomes are also comprised of (ii) a compound having the general structure:

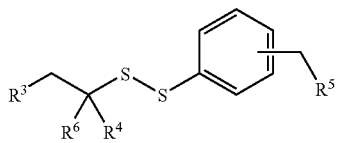

wherein $R^3$ is a hydrophilic polymer comprising a linkage for attachment to the dithiobenzyl moiety; $R^4$ is selected from the group consisting of H, alkyl and aryl; $R^5$ is selected from the group consisting of $O(C=O)R^7$, $S(C=O)R^7$, and $O(C=S)R^7$; $R^7$ comprises an amine-containing lipid; and $R^6$ is selected from the group consisting of H, alkyl and aryl; and where orientation of $CH_2$—$R^5$ is selected from the ortho position and the para position.

The liposomes also comprise, (b) an associated nucleic acid.

In one embodiment, X is NH and Y is oxygen. In another embodiment, L is a carbamate linkage, an ester linkage or a carbonate linkage. In yet another embodiment, L is NH—(C=O)—O—$CH_2$.

In another embodiment, Z is an imidazole. In yet another embodiment, Z is a moiety having a pK value between 5.0–6.5.

The liposome composition typically contains between 1–80 mole percent of the lipid.

In other embodiment, each of $R^1$ and $R^2$ is an unbranched alkyl or alkenyl chain having between 8–24 carbon atoms. For example, each of $R^1$ and $R^2$ can be $C_{17}H_{35}$.

In another embodiment, n is between 1–10.

In a further embodiment, $R^6$ is H and $R^4$ is selected from the group consisting of $CH_3$, $C_2H_5$ and $C_3H_8$. In another embodiment, $R^4$ and $R^6$ are alkyls.

The amine-containing lipid, in one embodiment, comprises either a single hydrocarbon tail or a double hydrocarbon tail. In another embodiment, the amine-containing lipid is a phospholipid having a double hydrocarbon tail.

The moiety $R^3$, in one embodiment, is selected from the group consisting of polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers thereof, and polyethyleneoxide-polypropylene oxide.

In a preferred embodiment, $R^3$ is polyethyleneglycol, $R^6$ is H and $R^4$ is $CH_3$ or $C_2H_5$.

Typically, the liposomes include between 5–20 mole percent of the compound.

It will be appreciated that the liposomes, in addition to being associated with a nucleic acid, can further include a therapeutic compound entrapped in the liposomes. The nucleic acid can be entrapped in at least a portion of the liposomes or can be externally associated with the liposomes. The nucleic acid can be DNA, RNA, fragments thereof, or a DNA or RNA oligonucleotide.

In another embodiment, the liposomes further include a ligand for targeting the liposomes to a target site. Typically, the ligand is covalently attached to a distal end of the hydrophilic polymer $R^3$ on the compound. In one embodiment, the ligand has binding affinity for endothelial tumor cells for internalization by such cells. Exemplary ligands include ligands suitable for binding to the following receptors: receptor for a c-erbB-2 protein product of the HER2/neu oncogene, epidermal growth factor (EGF) receptor, basic fibroblast growth receptor (basic FGF) receptor, vascular endothelial growth factor receptor, E-selectin receptor, L-selectin receptor, P-selectin receptor, folate receptor, CD4 receptor, CD19 receptor, αβ integrin receptors, and chemokine receptors. In preferred embodiment, the ligand is her2, FGF, folate, and E-selectin. It will be appreciated that the liposomes can include more than one type of ligand.

In another embodiment, the liposomes can further include a cationic lipid, as will be described.

These and other objects and features of the invention will be more fully appreciated when the following detailed description of the invention is read in conjunction with the accompanying drawings.

DETAILED DESCRIPTION OF THE INVENTION

I. Definitions

Figure 1:
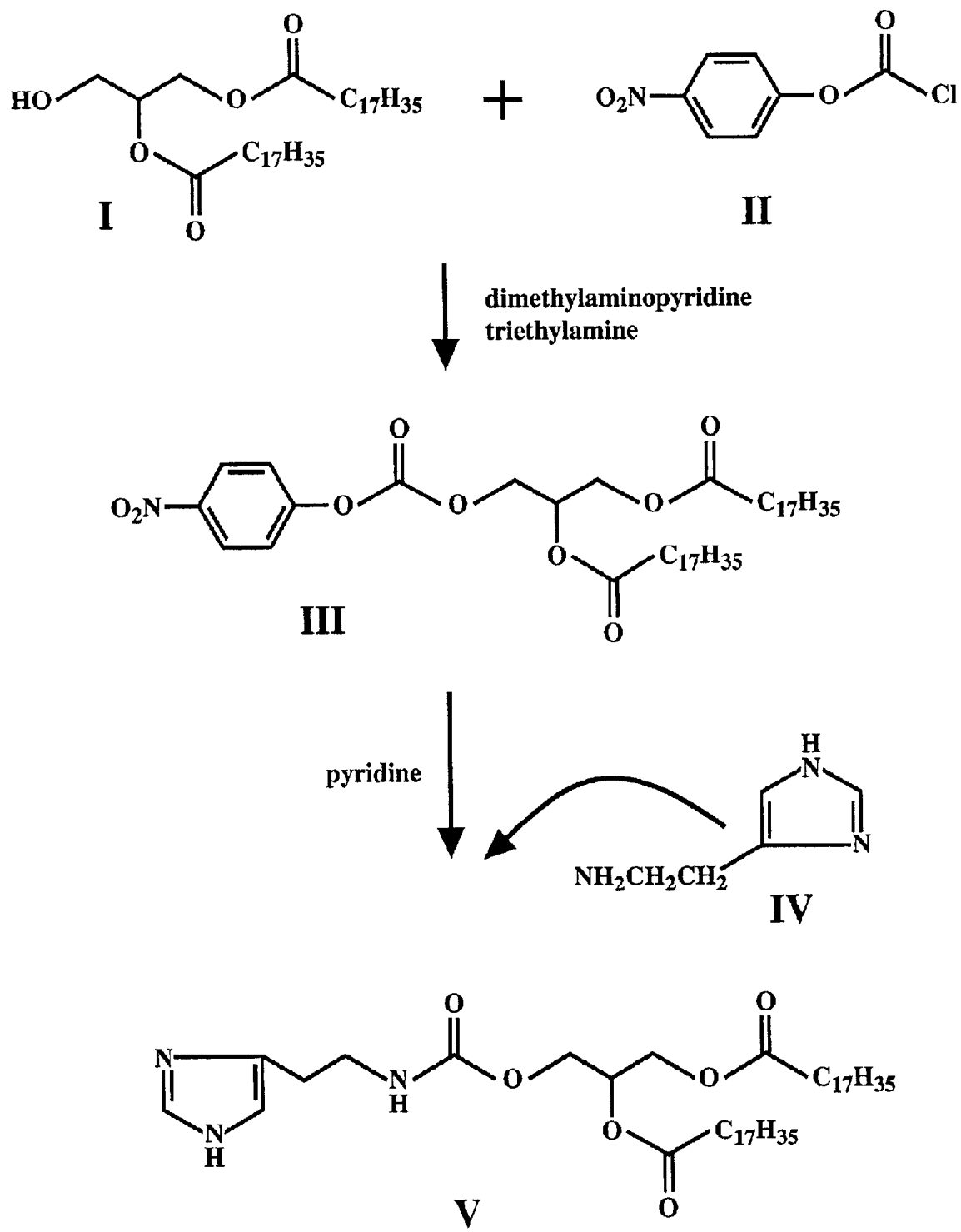
FIG. 1 shows a synthetic scheme for the preparation of a lipid in accordance with the invention having a carbamate linkage and an imidazole "Z" group.

The terms below have the following meanings unless indicated otherwise.

As used herein, a "neutral" lipid is one that is uncharged, having no ionic character.

A "charged" lipid is one having a positive or negative charge, having ionic character.

"Vesicle-forming lipids" refers to amphipathic lipids which have hydrophobic and polar head group moieties, and which can form spontaneously into bilayer vesicles in water, as exemplified by phospholipids, or are stably incorporated into lipid bilayers, with the hydrophobic moiety in contact with the interior, hydrophobic region of the bilayer membrane, and the polar head group moiety oriented toward the exterior, polar surface of the membrane. The vesicle-forming lipids of this type typically include one or two hydrophobic acyl hydrocarbon chains or a steroid group, and may contain a chemically reactive group, such as an amine, acid, ester, aldehyde or alcohol, at the polar head group.

Included in this class are the phospholipids, such as phosphatidyl choline (PC), phosphatidyl ethanolamine (PE), phosphatidic acid (PA), phosphatidyl inositol (PI), and sphingomyelin (SM), where the two hydrocarbon chains are typically between about 14–22 carbon atoms in length, and have varying degrees of unsaturation. Also included within the scope of the term "vesicle-forming lipids" are glycolipids, such as cerebrosides and gangliosides, and sterols, such as cholesterol.

"Alkyl" refers to a fully saturated monovalent radical containing carbon and hydrogen, and which may be branched or a straight chain. Examples of alkyl groups are methyl, ethyl, n-butyl, t-butyl, n-heptyl, and isopropyl. "Lower alkyl" refers to an alkyl radical of one to six carbon atoms, as exemplified by methyl, ethyl, n-butyl, i-butyl, t-butyl, isoamyl, n-pentyl, and isopentyl.

"Alkenyl" refers to monovalent radical containing carbon and hydrogen, which may be branched or a straight chain, and which contains one or more double bonds.

"Hydrophilic polymer" as used herein refers to a polymer having moieties soluble in water, which lend to the polymer some degree of water solubility at room temperature. Exemplary hydrophilic polymers include polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers of the above-recited polymers, and polyethyleneoxide-polypropylene oxide copolymers. Properties and reactions with many of these polymers are described in U.S. Pat. Nos. 5,395,619 and 5,631,018.

"Polymer comprising a reactive functional group" or "polymer comprising a linkage for attachment" refers to a polymer that has been modified, typically but not necessarily, at a terminal end moiety for reaction with another compound to form a covalent linkage. Reaction schemes to functionalize a polymer to have such a reactive functional group of moiety are readily determined by those of skill in the art and/or have been described, for example in U.S. Pat. No. 5,631,018 or by Zalipsky et al., in for example, *Eur. Polymer. J.*, 19(12):1177–1183 (1983); *Bioconj. Chem.*, 4(4):296–299 (1993).

"Fast-cleavable PEG" refers to an mPEG-DTB-lipid where $R^4$ and $R^6$ (see structure in Section IIB below) are hydrogen.

"Slow-cleavable PEG" refers to an mPEG-DTB-lipid where the dithiobenzyl moiety is hindered by attachment of an alkyl moiety at $R^4$ and/or $R^6$ (see structure in Section IIB below).

An "aliphatic disulfide" linkage intends a linkage of the form R'—S—S—R", where R' and R" are linear or branched alkyl chains that may be further substituted.

Abbreviations: PEG: polyethylene glycol; mPEG: methoxy-terminated polyethylene glycol; Chol: cholesterol; PC: phosphatidyl choline; PHPC: partially hydrogenated phosphatidyl choline; PHEPC: partially hydrogenated egg phosphatidyl choline; PHSPC: partially hydrogenated soy phosphatidyl choline; DSPE: distearoyl phosphatidyl ethanolamine; APD: 1-amino-2,3-propanediol; DTPA: diethylenetetramine pentaacetic acid; Bn: benzyl; NCL: neutral cationic liposome; FGF: fibroblast growth factor; HDSG: histamine distearoyl glycerol; DOTAP: 1,2-diolelyloxy-3-(trimethylamino) propane; DTB: dithiobenzyl; FC-PEG: fast-cleavable PEG; SC-PEG: slow-cleavable PEG; DDAB: dimethyldioctadecylammonium; GC33: $N^2$-[$N^2$, $N^5$-bis(3-aminopropyl)-L-ormithyl]-N,N-dioctadecyl-L-glutamine tetrahydrotrifluoroacetate; EtDTB, ethyl-dithiobenzyl; DOPE, dioleoyl phosphatidylethanolamine.

II. Liposome Components

In one aspect, the invention includes a liposome composition comprised of liposomes and a nucleic acid. The liposomes are of a "cationic-neutral lipid" and a lipid derivatized with a hydrophilic polymer through a releasable bond. These liposome components will now be described.

A. Cationic-Neutral Lipid

The cationic-neutral lipid included in the liposomes of the present invention is generally a lipid represented by the following structure:

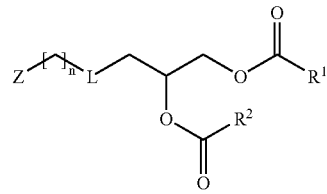

where each of $R^1$ and $R^2$ is an alkyl or alkenyl chain having between 8–24 carbon atoms; n=0–20 and in a preferred embodiment is between 1–10; L is selected from the group consisting of (i) —X—(C=O)—Y—[[CH$_2$—]], (ii) —X—(C=O)—, and (iii) —X—[[CH$_2$—]], where X and Y are independently selected from oxygen, NH and a direct bond; and Z is a weakly basic moiety that has a pK of less than 7.4 and greater than about 4.0.

In another embodiment, Z is a moiety having a pK value between 4.5–7.0, more preferably between 5–6.5, and most preferably between 5–6.

The weakly basic moiety Z results in a lipid that at physiologic pH of 7.4 is predominantly, e.g., greater than 50%, neutral in charge but at a selected pH value lower than physiologic pH tends to have a positive charge. By way of example, and in a preferred embodiment, Z is an imidazole moiety, which has a pK of about 6.0. At physiologic pH of 7.4, this moiety is predominantly neutral, but at pH values lower than 6.0, the moiety becomes predominantly positive. In support of the invention, a lipid having an imidazole moiety was prepared and used in preparation of liposomes, as will be discussed below.

In addition to imidazole, substituted imidazoles, as well as benzimidazoles and naphthimidazoles, can be used as the Z moiety in the structure given above, as long as the substitution does not alter the pKa to a value outside the desired range. Suitable substituents typically include alkyl, hydroxyalkyl, alkoxy, aryl, halogen, haloalkyl, amino, and aminoalkyl. Examples of such compounds reported to have pK's in the range of 5.0 to 6.0 include, but are not limited to, various methyl-substituted imidazoles and benzimidazoles, histamine, naphth[1,2-d]imidazole, 1H-naphth[2,3-d]imidazole, 2-phenylimidazole, 2-benzyl benzimidazole, 2,4-diphenyl-1H-imidazole, 4,5-diphenyl-1H-imidazole, 3-methyl-4(5)-chloro-1H-imidazole, 5(6)-fluoro-1H-benzimidazole, and 5-chloro-2-methyl-1H-benzimidazole.

Other nitrogen-containing heteroaromatics, such as pyridines, quinolines, isoquinolines, pyrimidines, phenanthrolines, and pyrazoles, can also be used as the Z group. Again, many such compounds having substituents selected from alkyl, hydroxyalkyl, alkoxy, aryl, halo, alkyl, amino, aminoalkyl, and hydroxy are reported to have pK's in the desired range. These include, among pyridines, 2-benzylpyridine, various methyl- and dimethylpyridines, as well as other lower alkyl and hydroxylalkyl pyridines, 3-aminopyridine, 4-(4-aminophenyl)pyridine, 2-(2-methoxyethyl)pyridine, 2-(4-aminophenyl)pyridine, 2-amino-4-chloropyridine, 4-(3-furanyl)pyridine, 4-vinylpyridine, and 4,4'-diamino-2,2'-bipyridine, all of which have reported pK's between 5.0 and 6.0. Quinolinoid compounds reported to have pK's in the desired range include, but are not limited to, 3-, 4-, 5-, 6-, 7- and 8-amino isoquinoline, various lower alkyl- and hydroxy-substituted quinolines and isoquinolines, 4-, 5-, 7- and 8-isoquinolinol, 5-, 6-, 7- and 8-quinolinol, 8-hydrazinoquinoline, 2-amino-4-methylquinazoline, 1,2,3,4-tetrahydro-8-quinolinol, 1,3-isoquinolinediamine, 2,4-quinolinediol, 5-amino-8-hydroxyquinoline, and quinuclidine. Also having pK's in the desired range are several amine-substituted pyrimidines, such as 4-(N,N-dimethylamino) pyrimidine, 4-(N-methylamino) pyrimidine, 4,5-pyrimidine diamine, 2-amino-4-methoxy pyrimidine, 2,4-diamino-5-chloropyrimidine, 4-amino-6-methylpyrimidine, 4-amino pyrimidine, and 4,6-pyrimidinediamine, as well as 4,6-pyrimidinediol. Various phenanthrolines, such as 1,10-, 1,8-, 1,9-, 2,8-, 2,9- and 3,7-phenanthroline, have pK's in the desired range, as do most of their lower alkyl-, hydroxyl-, and aryl-substituted derivatives. Pyrazoles which may be used include, but are not limited to, 4,5-dihydro-1H-pyrazole, 4,5-dihydro-4-methyl-3H-pyrazole, 1-hydroxy-1H-pyrazole, and 4-aminopyrazole.

Many nitrogen-substituted aromatics, such as anilines and naphthylamines, are also suitable embodiments of the group Z. Anilines and naphthylamines further substituted with groups selected from methyl or other lower alkyl, hydroxyalkyl, alkoxy, hydroxyl, additional amine groups, aminoalkyl, halogen, and haloalkyl are generally reported to have pKa's in the desired range. Other amine-substituted aromatics which can be used include 2-aminophenazine, 2,3-pyrazinediamine, 4- and 5-aminoacenaphthene, 3- and 4-amino pyridazine, 2-amino-4-methylquinazoline, 5-aminoindane, 5-aminoindazole, 3,3', 4,4'-biphenyl tetramine, and 1,2- and 2,3-diaminoanthraquinone.

Also included as embodiments of Z are certain acyclic amine compounds, such as N,N'-dimethylguanidine and various substituted hydrazines, such as trimethylhydrazine, tetramethylhydrazine, 1-methyl-1-phenylhydrazine, 1-naphthalenylhydrazine, and 2-, 3-, and 4-methylphenyl hydrazine, all of which are reported to have pKa' between 4.5 and 7.0. Alicyclic compounds having pKa's in this range include 1-pyrrolidineethanamine, 1-piperidineethanamine, hexamethylenetetramine, and 1,5-diazabicyclo[3,3,3]undecane.

Also suitable as the Z moiety in the structure given above are certain aminosugars, as will be described with respect to FIGS. 3C–3D discussed below.

The above listings give examples of compounds having pKa's between 4.5 and 7.0 which may be used as pH-responsive groups in the lipid conjugates of the invention; these listings are not intended to be limiting. In selected embodiments, the group Z is a imidazole, aniline, aminosugar or derivative thereof. Preferably, the effective pKa of the group Z is not significantly affected by its attachment to the lipid group. Examples of linked conjugates are given below.

The lipids of the invention include a neutral linkage L joining the Z moiety and the tail portion of the lipid. Linkage L is variable, and in preferred embodiments is selected from a carbamate, an ester, an urea amide, a carbonate, an amine, and an ether. In a preferred lipid prepared in support of the invention, a carbamate linkage, where L is —X—(C=O)—Y—[[CH$_2$—]], X being NH and Y being oxygen, was prepared.

In the tail portion of the lipid, $R^1$ and $R^2$ are the same or different and can be an unbranched alkyl or alkenyl chain having between 8–24 carbon atoms. More preferably, the $R^1$ and $R^2$ groups are between 12–22 carbon atoms in length, with $R^1=R^2=C_{17}H_{35}$ (such that the group is a stearyl group) or $R^1=R^2=C_{17}H_{33}$ (such that the group is an oleoyl group).

The lipid of the invention can be prepared using standard synthetic methods. As mentioned above, in studies performed in support of the invention, a lipid having the structure shown above, where Z is an imidazole, n=2, L is a carbamate and $R^1=R^2=C_{17}H_{35}$, was prepared. A reaction scheme for preparation of the exemplary lipid is illustrated in FIG. 1 and details of the synthesis are provided in Example 1. Briefly, the para-nitrophenyl carbonate of 1,2-distearoyl glycerol (Compound III) was prepared from 1,2-distearoyl-sn-glycerol (Compound I) and para-nitrophenyl chloroformate (Compound II) and reacted with histamine (Compound IV) to yield a lipid (Compound V) having a imidazole moiety linked to a distearoyl tail via a carbamate linkage. A similar route, using glycerol in place of 1-amino-2,3-propanediol, can be used to produce a carbonate-linked product (L=—O—(C=O)—O—CH$_2$—).

Figure 2A:
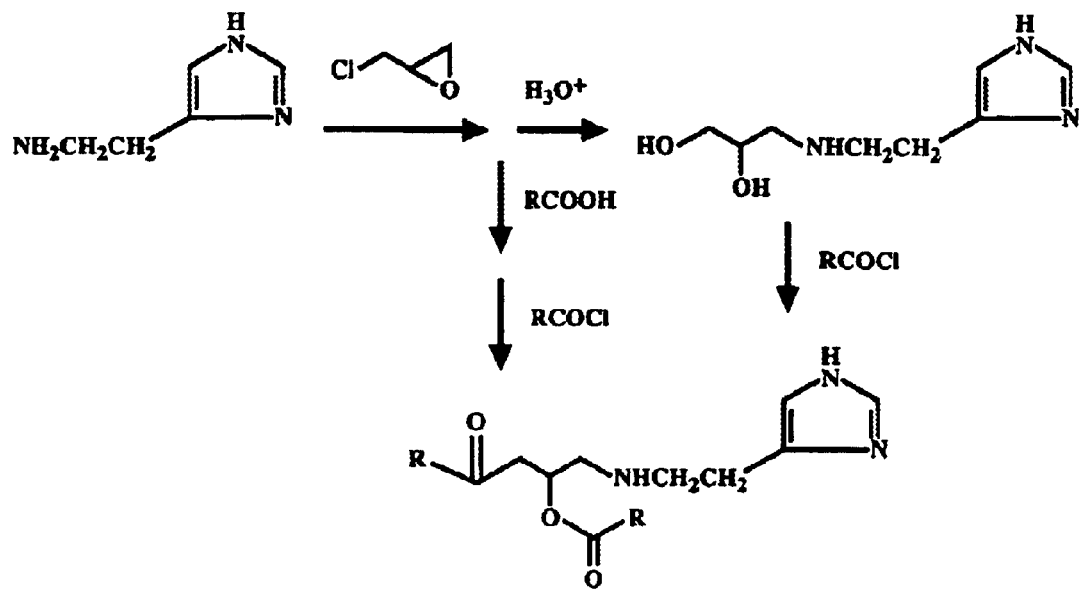
FIGS. 2A–2D show synthetic reaction schemes for preparation of pH responsive lipids in accord with the invention.
Figure 2B:
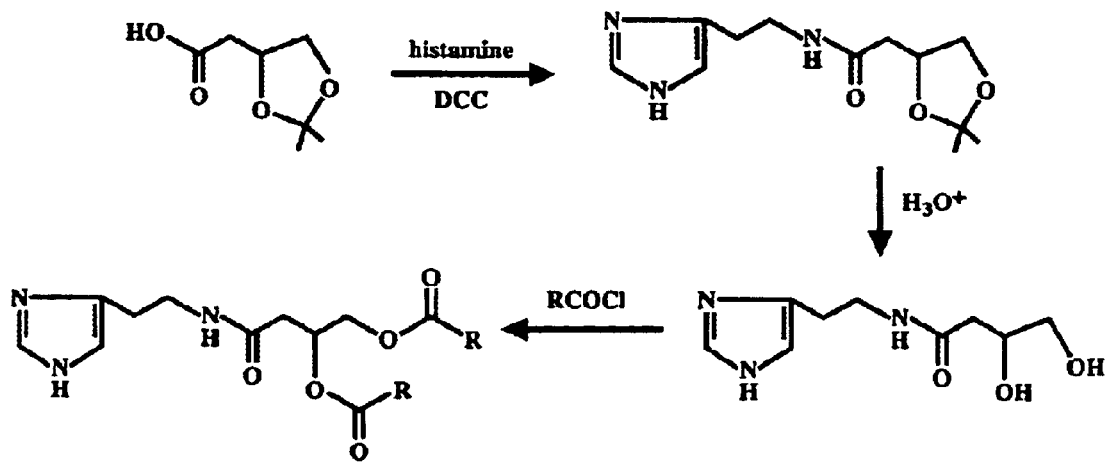

Preparation of the lipid having other linkages is readily done by those of skill in the art using conventional methods. Other linkages include ether (L=—O—CH$_2$—) and ester linkages (L=—O—(C=O)—), as well as urea amide, and amine linkages (i.e., where L=—NH—(C=O)—NH—, —NH—(C=O)—[[CH$_2$—]], [[—NH—(C=O)—NH—CH$_2$—]], or —NH—[[CH$_2$—]]). A keto linkage, where X is a direct bond, is also possible. FIGS. 2A–2B illustrate preparation of an amine-linked lipid (FIG. 2A) and lipid having an NH— containing linkage (FIG. 2B). In FIG. 2A, the terminal amine of histamine is reacted with glycidyl chloride, the resulting epoxide is hydrolyzed, and the resulting diol is acylated.

In FIG. 2B, lipid having an NH— containing linkage is prepared, for example, by reacting histamine with an activated derivative of glyceric acid acetonide (2,2-dimethyl-1,3-dioxolane-4-carboxylic acid) or the four-carbon homolog, 2,2-dimethyl-1,3-dioxolane-4-acetic acid, as shown. The diol is then deprotected and acylated.

Figure 2C:
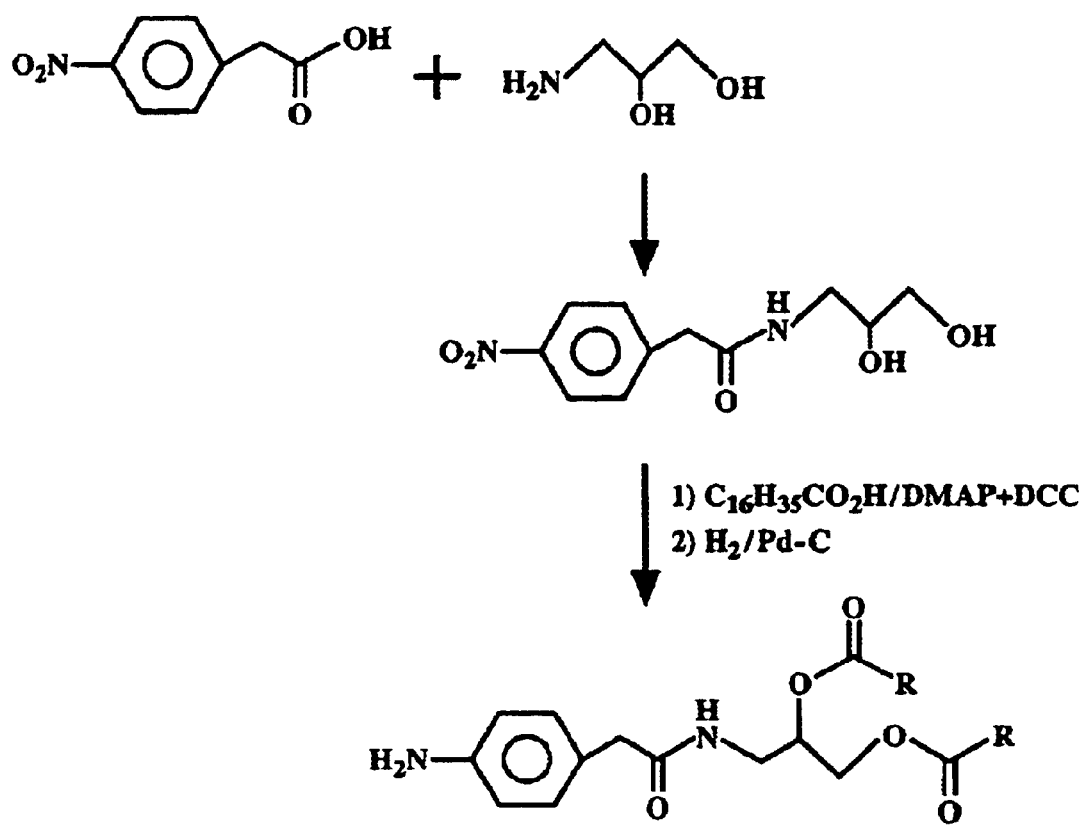
Figure 2D:
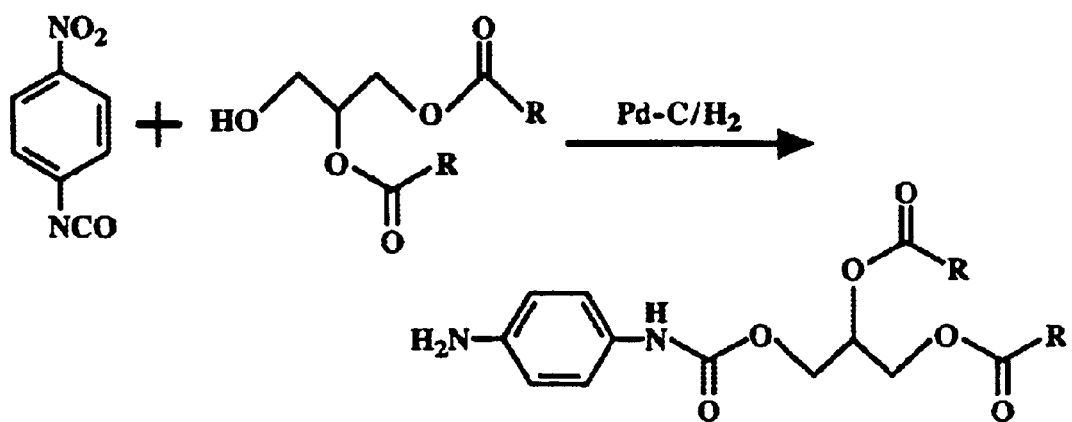
Figure 4:
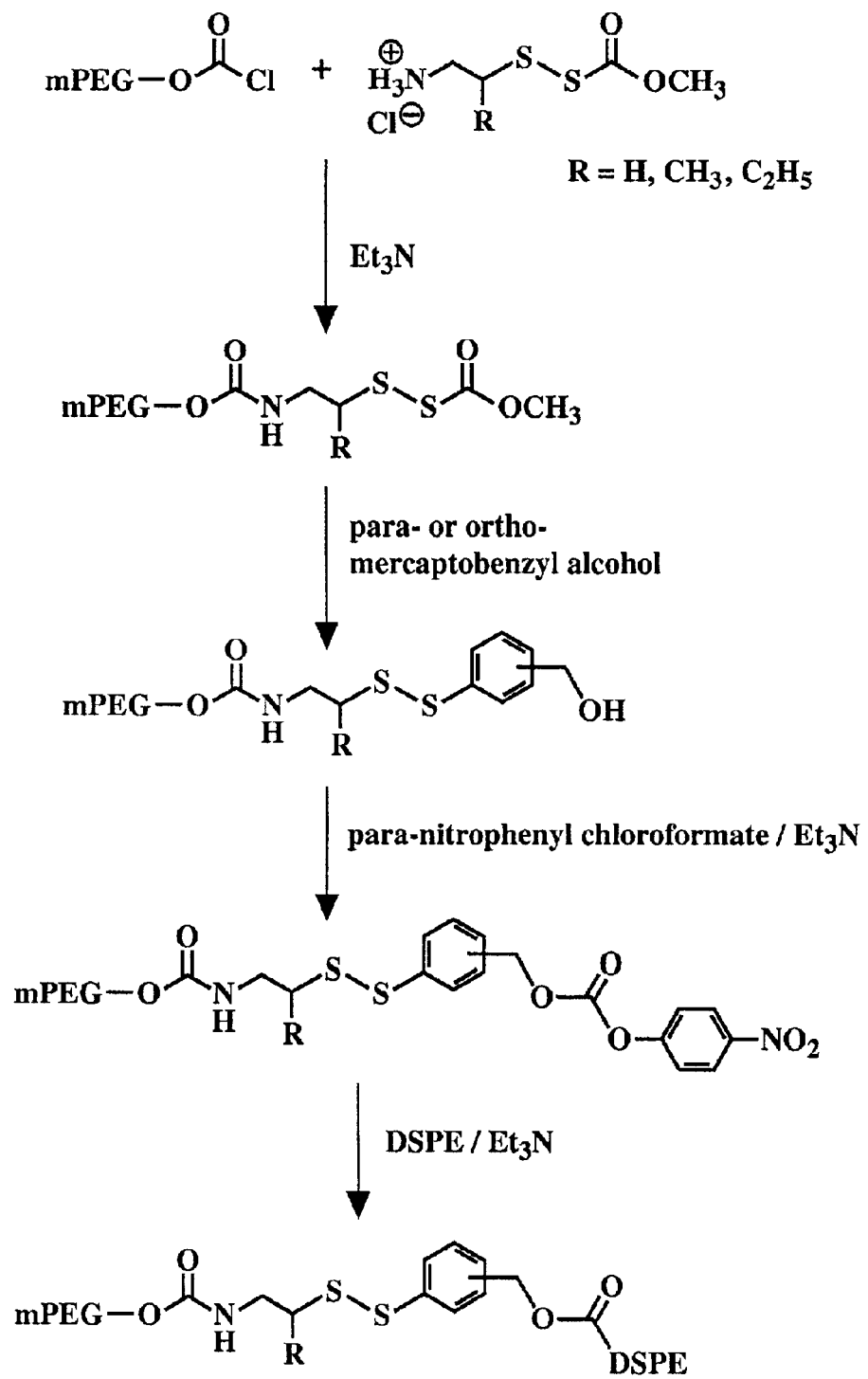
FIG. 4 illustrates a synthetic reaction scheme for synthesis of the mPEG-DTB-amine-lipid, where the amine-ligand is the lipid distearoylphosphatidylethanolamine (DSPE)

FIGS. 2C and 2D show other reaction schemes for preparation of pH-responsive lipids in accord with the invention. In FIG. 2C, 4-nitrobenzoic acid is condensed with 1-amino-2,3-propanediol, giving an amide linkage; the diol is acylated and the nitro group reduced to an amine to give the product, a lipid-aniline conjugate. In FIG. 2D, the initial condensation reaction is between an alcohol (diacylglycerol) and an isocyanate, giving a carbamate linkage in the product.

Figure 3A:
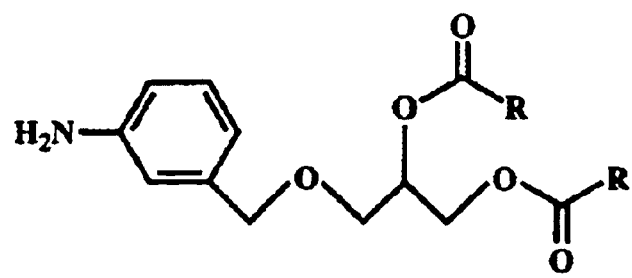
FIGS. 3A–3D show various structures of pH responsive lipids in accord with the invention.
Figure 3B:
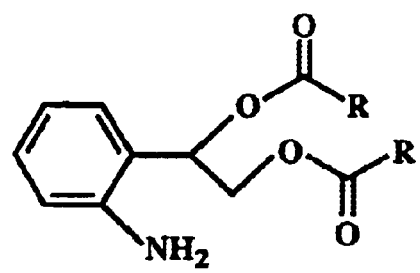
Figure 3C:
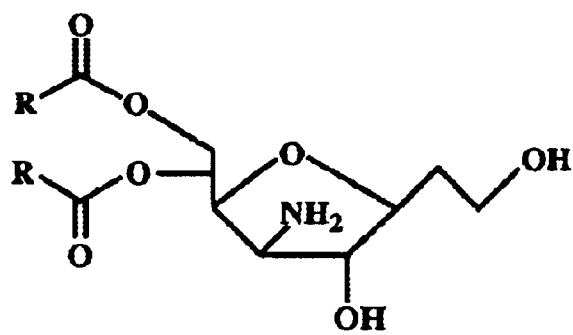
Figure 3D:
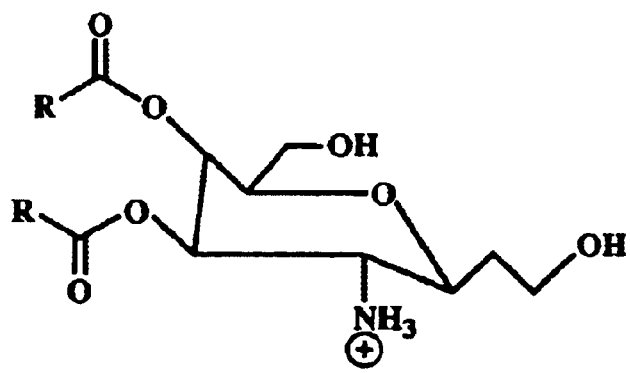

FIGS. 3A–3D show various structures of pH-responsive lipids in accord with the invention, where FIGS. 3A–3B show further lipids having an aromatic amine as the "Z" moiety, and FIGS. 3C–3D show lipids having an aminosugar attached to a lipid. Synthesis of these lipids can be readily performed by those of skill in the art using commercially available starting materials. For example, the product of FIG. 3A may be prepared by reaction of m-nitrobenzyl bromide and a diacylglycerol, giving the ether linkage, followed by reduction of the nitro group. The product of FIG. 3B is prepared from commercially available (2-nitrophenyl)-1,2-ethanediol by acylation of the diol and reduction of the nitro group. To prepare the aminosugar-lipid conjugate shown in FIG. 3C, D-glucose (furanose form) is protected by reaction with two molecules of acetone, and the free hydroxyl group is sequentially reacted with TsCl, sodium azide, and iodine to give an intermediate nitro compound. The exocyclic diol is deprotected and acylated, and the nitro group reduced to the amine. The compound of FIG. 3D can be prepared in a similar manner from D-galactose.

In a preferred embodiment, the pH-dependent lipid is histamine-distearoyl glycerol (HDSG). The imidazole of histamine has a pKa of 6. HDSG tends to be neutral at physiological pH (pH 7.4), and is predominantly positively charged at a pH lower than 6.

HDSG-incorporated liposomes encapsulate DNA at about pH 4 to 5, similar to conventional cationic liposomes. The surface charge of the HDSG liposome/complex is reduced at physiological pH in the blood circulation. The surface charge of HDSG is predominantly positive charge at pH 5 to 6 (the consensus pH in endosome and lysosome) to facilitate the interaction of the complexes with the lysosomal membrane and release of the nucleic acid content into the cytoplasm.

B. Lipid-DTB-Polymer

The liposomes of the invention also include a lipid derivatized with a hydrophilic polymer via a releasable bond, such as a dithiobenzyl moiety. This lipid-polymer component has the general structure:

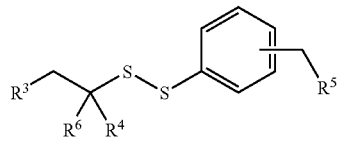

wherein $R^3$ comprises a hydrophilic polymer including a functional group suitable for covalently attaching the polymer to the dithiobenzyl moiety. $R^4$ and $R^6$ are independently selected to be H, an alkyl or an aryl, and can be varied to tailor the rate of disulfide cleavage. For example, to achieve a faster rate of cleavage, $R^4$ and $R^6$ are hydrogen. A slower rate of cleavage is achieved by sterically hindering the disulfide by selecting an alkyl or aryl for one or both of $R^4$ and $R^6$. $R^5$ comprises a linking moiety joined to $R^7$, which comprises an amine-containing lipid. The linking moiety in preferred embodiments is O(C=O), S(C=O) or O(C=O). The amine-containing lipid $R^7$ can be a primary or a secondary amine and can be selected from any number of lipids, including those described below. The orientation of the group $CH_2$—$R^5$ can be either ortho or para.

The amine-containing lipid $R^7$ is typically a water-insoluble molecule having at least one acyl chain containing at least about eight carbon atoms, more preferably an acyl chain containing between about 8–24 carbon atoms. A preferred lipid is a lipid having an amine-containing polar head group and an acyl chain. Exemplary lipids are phospholipids having a single acyl chain, such as stearoylamine, or two acyl chains. Preferred phospholipids with an amine-containing head group include phosphatidylethanolamine and phosphatidylserine. The lipid tail(s) can have between about 12 to about 24 carbon atoms and can be fully saturated or unsaturated. One preferred lipid is distearoylphosphatidylethanolamine (DSPE), however those of skill in the art will appreciate the wide variety of lipids that fall within this description. It will also be appreciated that the lipid can naturally include an amine group or can be derivatized to include an amine group. Other lipid moieties that do not have an acyl tail, such as cholesterolamine, are also suitable.

Synthesis of a polymer-DTB-lipid compound is schematically depicted in FIG. 4. mPEG derivatives (MW 2000 and 5000 Daltons) having a methoxycarbonyldithioalkyl end group were prepared by reacting 2-(methoxycarbonyldithio) ethaneamine with mPEG-chloroformate, which was readily prepared by phosgenation of dried mPEG-OH solution (Zalipsky, S., et al., *Biotechnol. Appl. Biochem.* 15:100–114 (1992).). The former compound was obtained through 2-aminoethanethiol hydrochloride reaction with an equivalent amount of methoxycarbonylsulfenyl chloride, according to published procedures (Brois, S. J., et al., *J. Amer. Chem. Soc.* 92:7629–7631 (1970); Koneko, T., et al., *Bioconjugate Chem.* 2:133–141 (1991)). Both the para and ortho isomers of mercaptobenzyl alcohol (Grice, R., et al., *J. Chem. Soc.* 1947–1954 (1963)) coupled cleanly with the resulting PEG-linked acyldisulfide, yielding mPEG bearing a dithio benzyl alcohol end group. Active carbonate introduction proceeded as with underivatized mPEG-OH, to give the para-nitrophenyl carbonate. Addition of DSPE in ethanolamine formed the desired mPEG-DTB-DSPE product. Both ortho- and para-DTB-lipid compounds were prepared and purified by silica gel chromatography and characterized by NMR and MALDI-TOFMS, the details of which are given in Example 2.

Figure 5:
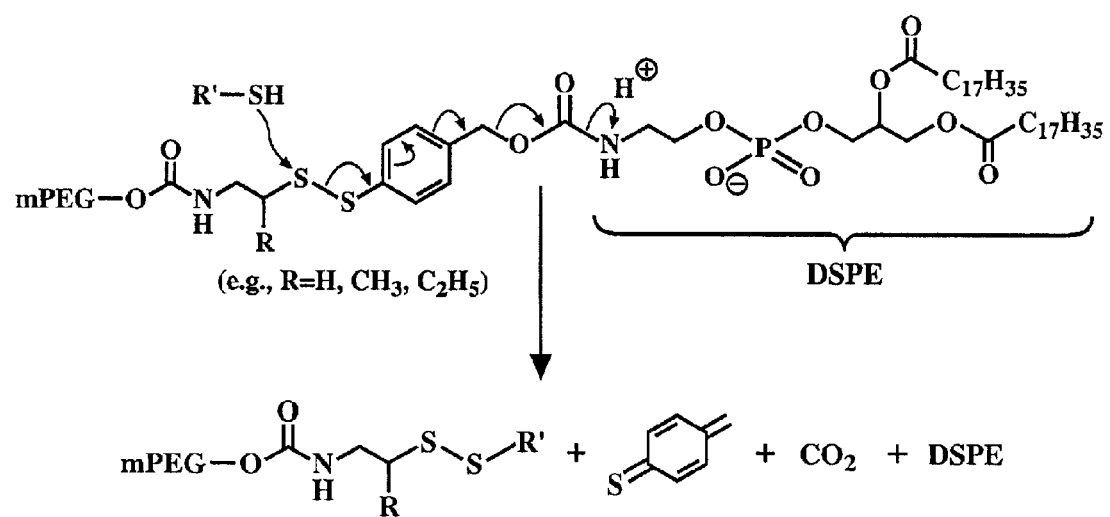
FIG. 5 illustrates the thiolytic cleavage mechanism of a para-dithiobenzyl urethane (DTB)-linked mPEG-DSPE conjugate.

FIG. 5 shows the mechanism of thiolytic cleavage of the mPEG-DTB-DSPE conjugate. Upon cleavage, the phosphatidylethanolamine lipid is regenerated in its natural, unmodified form.

Figure 6A:
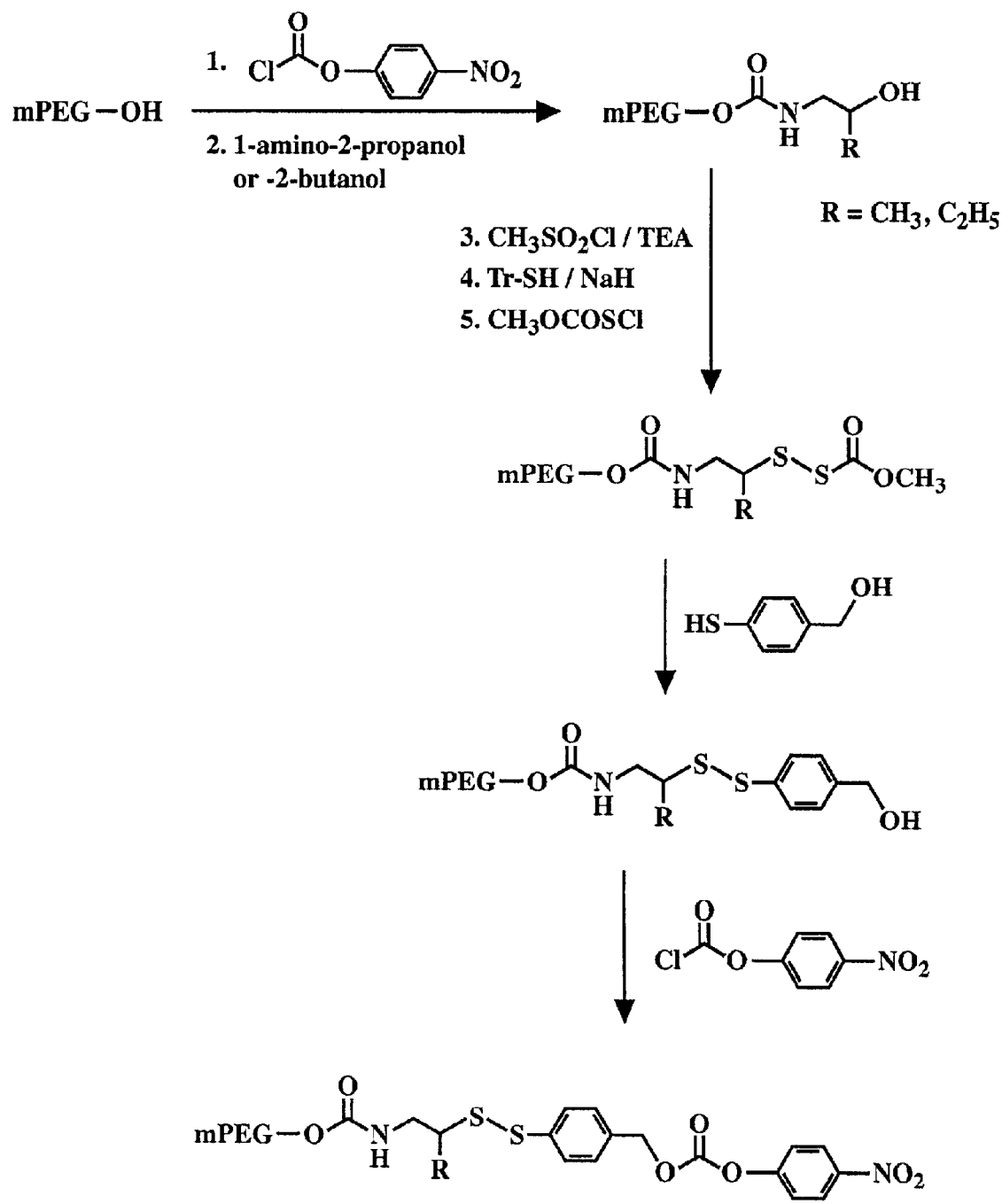
FIGS. 6A–6B show a synthetic reaction scheme for preparation of an mPEG-DTB-DSPE compound in accord with the invention where the DTB linkage is sterically hindered by an alkyl group.
Figure 6B:
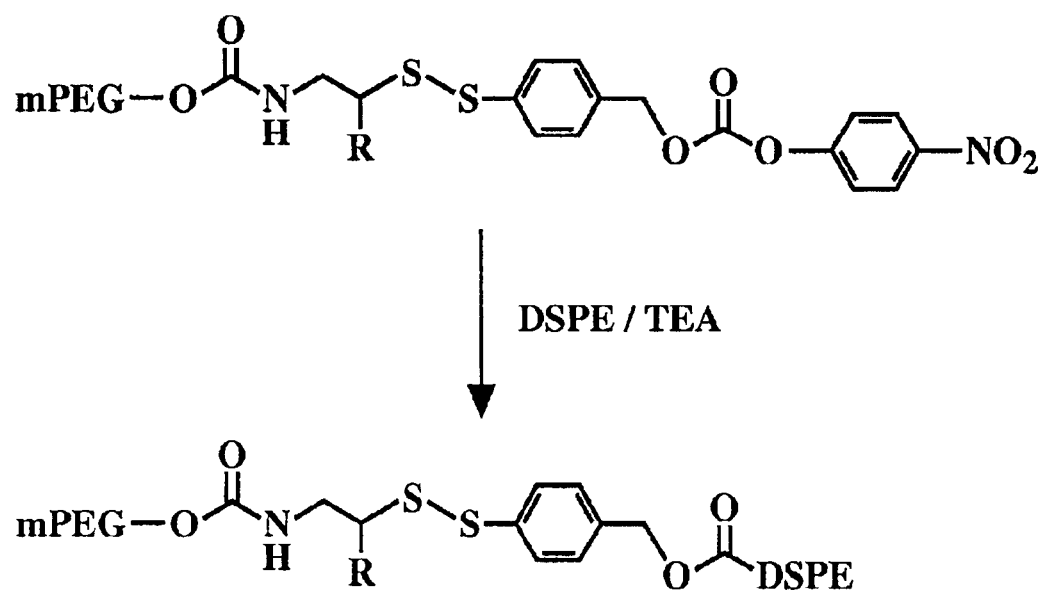

FIGS. 6A–6B show a reaction scheme for synthesis of mPEG-DTB-DSPE conjugates having an alkyl group adjacent the disulfide linkage, e.g., a more hindered disulfide linkage. As described more fully in Example 3A, mPEG-OH in dichloromethane was reacted with p-nitrophenylchloroformate in the presence of triethylamine (TEA) to form mPEG-nitrophenyl carbonate. An amino alcohol, such as 1-amino-2-propanol or 1-amino-2-butanol, in dimethylformamide (DMF) was reacted with the mPEG-nitrophenyl carbonate in the presence of TEA to form a secondary alcohol attached to PEG. The secondary alcohol was then converted to the desired mPEG-DTB-DSPE compound as illustrated in FIG. 6A and detailed in Example 3A.

In this reaction scheme, mPEG-methyl-dithiobenzyl-nitrophenyl chloroformate was reacted with DSPE to form the desired compound. The nitrophenyl chloroformate moiety in the mPEG-methyl-dithiobenzyl-nitrophenyl chloroformate compound acts as a leaving group to yield the desired product upon reaction with a selected lipid. The compound can also be produced by reaction with a compound such as mPEG-methyl-dithiobenzyl-$R^3$, where $R^3$ represents a leaving group joined through a linking moiety to the benzene ring. The leaving group is displaced upon reaction with an amine-containing ligand, such as DSPE, a polypeptide or an amine-containing drug. The leaving group is selected according to the reactivity of the amine in the ligand, and is preferably derived from various acidic alcohols that have a hydroxy- or oxy-containing leaving group. These include chloride, p-nitrophenol, o-nitrophenol, N-hydroxy-tetrahydrophthalimide, N-hydroxysuccinimide, N-hydroxy-glutarimide, N-hydroxynorbornene-2,3-dicarboxyimide, 1-hydroxybenzotriazole, 3-hydroxypyridine, 4-hydroxypyridine, 2-hydroxypyridine, 1-hydroxy-6-trifluoromethylbenzotriazole, imidazole, triazole, N-methyl-imidazole, pentafluorophenol, trifluorophenol and trichlorophenol.

Example 3B describes preparation of an mPEG-EtDTB-lipid conjugate where the disulfide linkage is hindered by an ethyl moiety.

Figure 7:
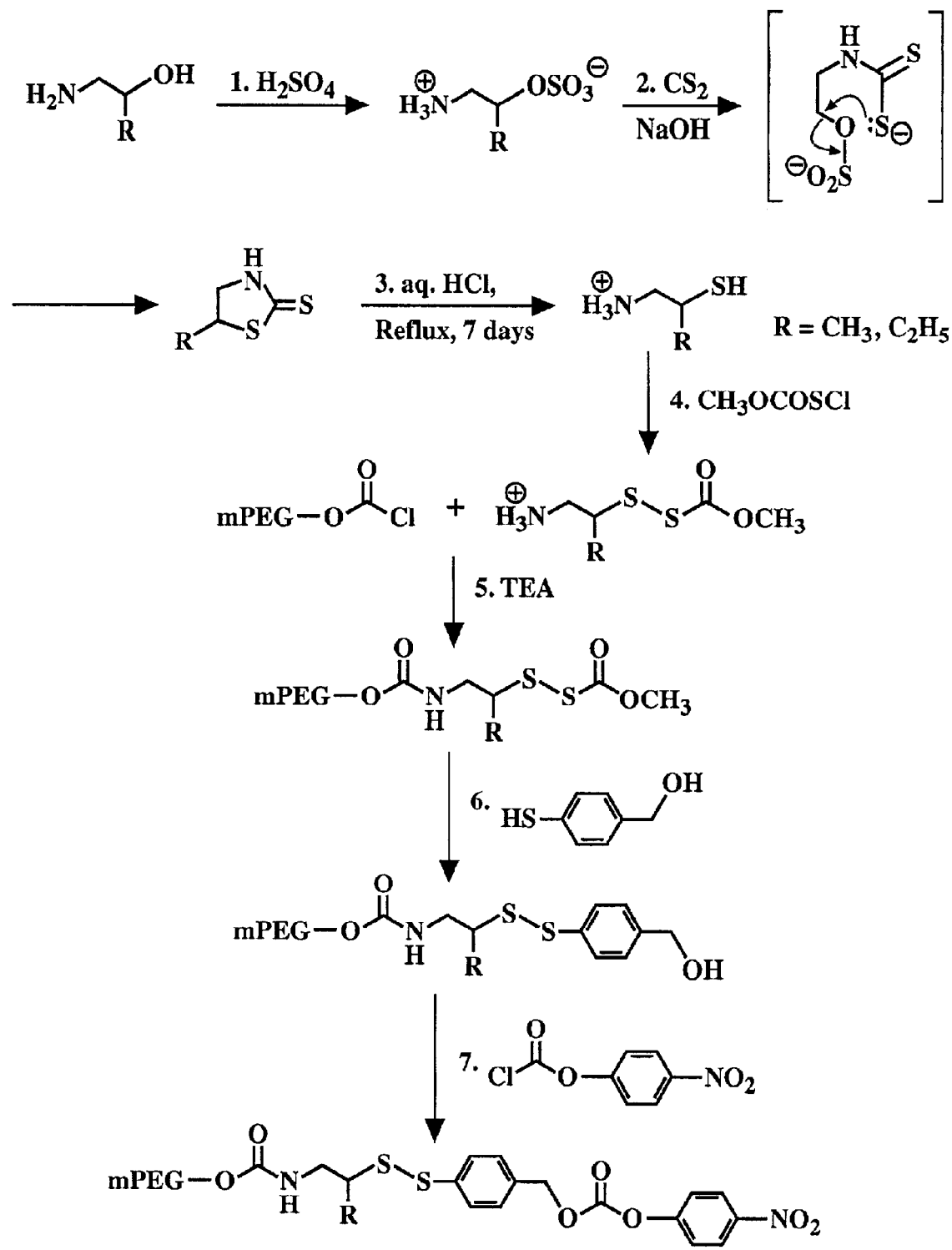
FIG. 7 shows another synthetic reaction scheme for preparation of an mPEG-DTB-ligand compound in accord with the invention.

FIG. 7 shows another synthetic reaction scheme for preparation of an mPEG-DTB-ligand compound in accord with the invention. The details of the reaction procedure are given in Examples 4A–4B. Briefly, cold 1-amino-2-propanol was reacted with sulfuric acid to form 2-amino-1methylethyl hydrogen sulfate. This product was reacted with carbon disulfide and sodium hydroxide in aqueous ethanol to yield 5-methylthiazolidine-2-thione. An aqueous solution of hydrochloric acid was added to the 5-methylthiazolidine-2-thione and heated. After refluxing for one week, the product, 1-mercapto(methyl)ethyl ammonium chloride, was crystallized and recovered. This product was reacted with methoxy carbonylsulfenyl chloride to yield 2-(methoxycarbonyldithio)ethaneamine. Reaction of the 2-(methoxycarbonyldithio)ethaneamine with mPEG-chloroformate using the procedure described above with respect to FIG. 4 yields the desired mPEG-DTB-nitrophenyl compound suitable for reaction with a selected amine-containing lipid.

Example 4B describes the reaction for synthesis of mPEG-(ethyl) DTB-nitrophenyl.

Figure 8A:
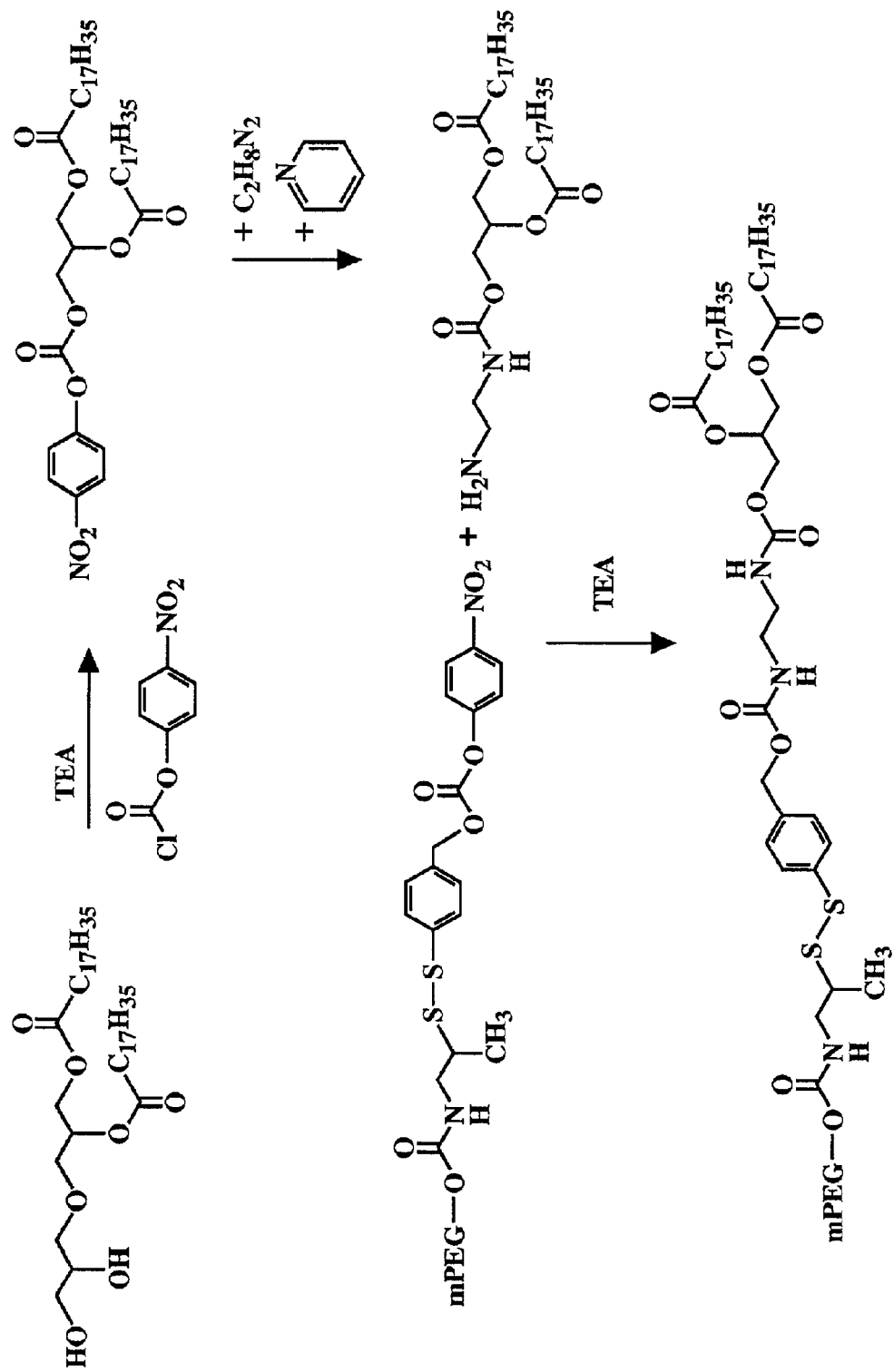
FIG. 8A is a synthetic reaction scheme for synthesis of an mPEG-DTB-lipid which upon thiolytic cleavage yields a cationic lipid.
Figure 8B:
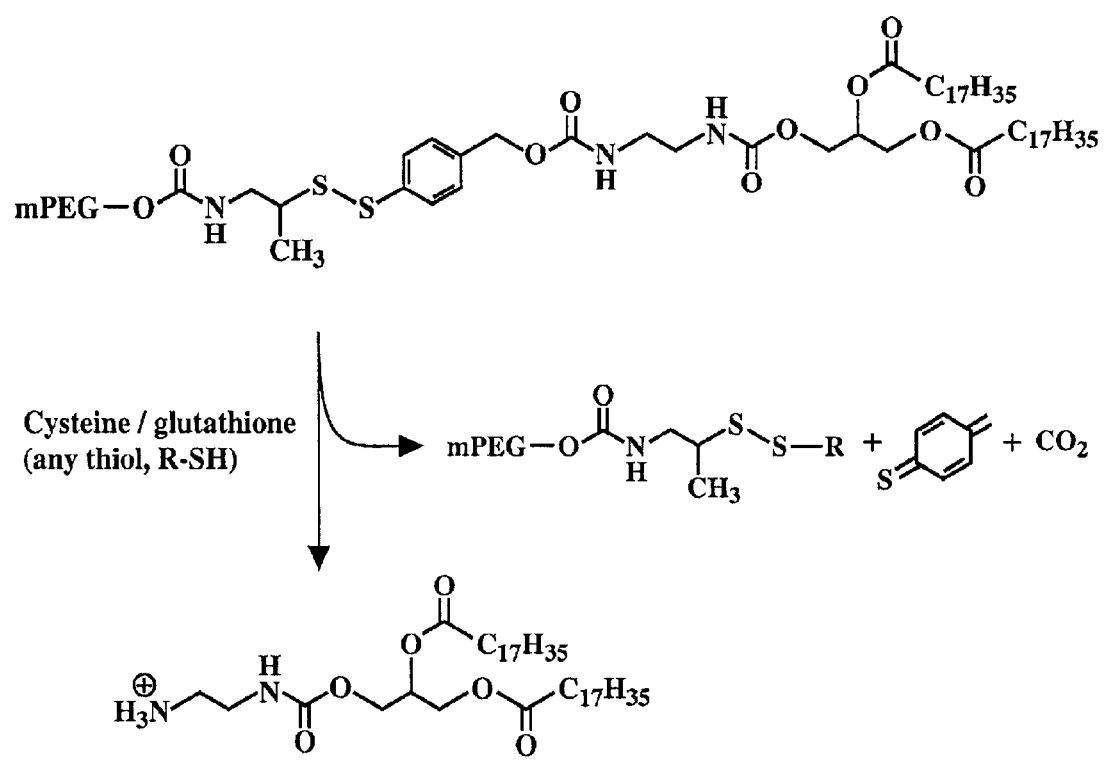
FIG. 8B shows the products after thiolytic cleavage of the compound in FIG. 8A.

FIG. 8A shows a reaction scheme for preparation of another mPEG-DTB-lipid compound in accord with the invention. The reaction details are provided in Example 5. The lipid 1,2-distearoyl-sn-glycerol is activated for reaction with mPEG-DTB-nitropheynl, prepared as described in FIG. 6A or FIG. 7. The resulting mPEG-DTB-lipid differs from the compounds described above in the absence of a phosphate head group. The mPEG-DTB-lipid of FIG. 8A is neutral prior to cleavage. As shown in FIG. 8B, upon thiolytic reduction of the disulfide bond, the compound decomposes to yield a cationic lipid. The positively-charged lipid provides for electrostatic interaction in vivo and commensurate advantages in in vivo targeting.

In the reaction schemes described above, $R^6$ of the claimed compound is H. However, in other embodiments $R^6$ is an alkyl or an aryl moiety. In this approach, for example where $R^4$ and $R^6$ are both $CH_3$ moieties, an α,β-unsaturated acyl chloride (R'R"C=CHCOCl, where R' is, for example $CH_3$ and R" is $CH_3$, however any alkyl or aryl is contemplated) is reacted with an amine-terminated PEG to give the corresponding N-PEG-substituted α,β-unsaturated amide. This compound is reacted with thiolacetic acid, giving the corresponding N-PEG-substituted β-(acetylthio) amide via conjugate addition to the C=C bond. The acetylthio group (—SCOCH$_3$) is hydrolyzed to a thiol group (—SH), which is then reacted with methyl (chlorosulfenyl) formate (ClSCOOCH$_3$), generating a methoxycarbonyl diothio group (—SSCOOCH$_3$); this intermediate is then reacted with p-mercapto benzyl alcohol to give the N-PEG-substituted β-(dithiobenzyl alcohol) amide (having the structure PEG—NH—CO—CH$_2$CR'R"-SS-p-phenyl-CH$_2$OH). The benzyl alcohol moiety is then reacted with nitrophenyl chloroformate to give the nitrophenyl carbonate leaving group, as above.

As will be described below, liposomes comprised of the cationic-neutral lipid and the polymer-DTB-lipid were prepared in studies in support of the invention.

C. Nucleic Acid

In a preferred embodiment of the invention, the liposomes formed of the lipids described above are associated with a nucleic acid. By "associated" it is meant that a therapeutic agent, such as a nucleic acid, is entrapped in the liposomes central compartment and/or lipid bilayer spaces, is associated with the external liposome surface, or is both entrapped internally and externally associated with the liposomes. It will be appreciated that the therapeutic agent can be a nucleic acid or a drug compound. It will also be appreciated that a drug compound can be entrapped in the liposomes and a nucleic acid externally associated with the liposomes, or vice versa.

In a preferred embodiment of the invention, a nucleic acid is associated with the liposomes. The nucleic acid can be selected from a variety of DNA and RNA based nucleic acids, including fragments and analogues of these. A variety of genes for treatment of various conditions have been described, and coding sequences for specific genes of interest can be retrieved from DNA sequence databanks, such as GenBank or EMBL. For example, polynucleotides for treatment of viral, malignant and inflammatory diseases and conditions, such as, cystic fibrosis, adenosine deaminase deficiency and AIDS, have been described. Treatment of cancers by administration of tumor suppressor genes, such as APC, DPC4, NF-1, NF-2, MTS1, RB, p53, WT1, BRCA1, BRCA2 and VHL, are contemplated.

Examples of specific nucleic acids for treatment of an indicated conditions include: HLA-B7, tumors, colorectal carcinoma, melanoma; IL-2, cancers, especially breast cancer, lung cancer, and tumors; IL-4, cancer; TNF, cancer; IGF-1 antisense, brain tumors; IFN, neuroblastoma; GM-CSF, renal cell carcinoma; MDR-1, cancer, especially advanced cancer, breast and ovarian cancers; and HSV thymidine kinase, brain tumors, head and neck tumors, mesothelioma, ovarian cancer.

The polynucleotide can be an antisense DNA oligonucleotide composed of sequences complementary to its target, usually a messenger RNA (mRNA) or an mRNA precursor. The mRNA contains genetic information in the functional, or sense, orientation and binding of the antisense oligonucleotide inactivates the intended mRNA and prevents its translation into protein. Such antisense molecules are determined based on biochemical experiments showing that proteins are translated from specific RNAs and once the sequence of the RNA is known, an antisense molecule that will bind to it through complementary Watson-Crick base pairs can be designed. Such antisense molecules typically contain between 10–30 base pairs, more preferably between 10–25, and most preferably between 15–20.

The antisense oligonucleotide can be modified for improved resistance to nuclease hydrolysis, and such analogues include phosphorothioate, methylphosphonate, phosphodiester and p-ethoxy oligonucleotides (WO 97/07784).

The entrapped agent can also be a ribozyme, DNAzyme, or catalytic RNA.

The nucleic acid or gene can, in another embodiment, be inserted into a plasmid, preferably one that is a circularized or closed double-stranded molecule having sizes preferably in the 5–40 Kbp (kilo basepair) range. Such plasmids are constructed according to well-known methods and include a therapeutic gene, i.e., the gene to be expressed in gene therapy, under the control of suitable promoter and enhancer, and other elements necessary for replication within the host cell and/or integration into the host-cell genome. Methods for preparing plasmids useful for gene therapy are widely known and referenced.

Polynucleotides, oligonucleotides, other nucleic acids, such as a DNA plasmid, can be entrapped in the liposome by passive entrapment during hydration of the lipid film. Other procedures for entrapping polynucleotides include condensing the nucleic acid in single-molecule form, where the nucleic acid is suspended in an aqueous medium containing protamine sulfate, spermine, spermidine, histone, lysine, mixtures thereof, or other suitable polycationic condensing agent, under conditions effective to condense the nucleic acid into small particles. The solution of condensed nucleic acid molecules is used to rehydrate a dried lipid film to form liposomes with the condensed nucleic acid in entrapped form.

D. Targeting Ligand

The liposomes may optionally be prepared to contain surface groups, such as antibodies or antibody fragments, small effector molecules for interacting with cell-surface receptors, antigens, and other like compounds, for achieving desired target-binding properties to specific cell populations. Such ligands can be included in the liposomes by including in the liposomal lipids a lipid derivatized with the targeting molecule, or a lipid having a polar-head chemical group that can be derivatized with the targeting molecule in preformed liposomes. Alternatively, a targeting moiety can be inserted into preformed liposomes by incubating the preformed liposomes with a ligand-polymer-lipid conjugate.

Lipids can be derivatized with the targeting ligand by covalently attaching the ligand to the free distal end of a hydrophilic polymer chain, which is attached at its proximal end to a vesicle-forming lipid. There are a wide variety of techniques for attaching a selected hydrophilic polymer to a selected lipid and activating the free, unattached end of the polymer for reaction with a selected ligand, and in particular, the hydrophilic polymer polyethyleneglycol (PEG) has been widely studied (Allen, T. M., et al., *Biochemicia et Biophysica Acta* 1237:99–108 (1995); Zalipsky, S., *Bioconjugate Chem.*, 4(4):296–299 (1993); Zalipsky, S., et al., *FEBS Lett.* 353:71–74 (1994); Zalipsky, S., et al., *Bioconjugate Chemistry*, 705–708 (1995); Zalipsky, S., in *Stealth Liposomes* (D. Lasic and F. Martin, Eds.) Chapter 9, CRC Press, Boca Raton, Fla. (1995)).

Targeting ligands are well known to those of skill in the art, and in a preferred embodiment of the present invention, the ligand is one that has binding affinity to endothelial tumor cells, and which is, more preferably, internalized by the cells. Such ligands often bind to an extracellular domain of a growth factor receptor. Exemplary receptors include the c-erbB-2 protein product of the HER2/neu oncogene, epidermal growth factor (EGF) receptor, basic fibroblast growth receptor (basic FGF) receptor and vascular endothelial growth factor receptor, E-, L- and P-selectin receptors, folate receptor, CD4 receptor, CD19 receptor, $\alpha\beta$ integrin receptors and chemokine receptors.

III. Preparation of the Composition

A. Liposome Component

Liposomes containing the lipids described above, that is, the cationic-neutral lipid and the polymer-DTB-lipid, can be prepared by a variety of techniques, such as those detailed in Szoka, F., Jr., et al., *Ann. Rev. Biophys. Bioeng.* 9:467 (1980), and specific examples of liposomes prepared in support of the present invention will be described below. Typically, the liposomes are multilamellar vesicles (MLVs), which can be formed by simple lipid-film hydration techniques. In this procedure, a mixture of liposome-forming lipids of the type detailed below are dissolved in a suitable organic solvent which is then evaporated in a vessel to form a thin film. The lipid film is then covered by an aqueous medium, hydrating to form MLVs, typically with sizes between about 0.1 to 10 microns.

Liposomes for use in the composition of the invention include (i) the neutral-cationic lipid and (ii) a lipid covalently attached to a hydrophilic polymer through a DTB linkage. The liposomes can also include other components, such as vesicle-forming lipids or a lipid that is stably incorporated into the liposome lipid bilayer, such as diacylglycerols, lyso-phospholipids, fatty acids, glycolipids, cerebrosides and sterols, such as cholesterol.

Typically, liposomes are comprised of between about 10–90 mole percent of the neutral-cationic lipid, more preferably between about 20–80 mole percent, and still more preferably between about 30–70 mole percent. The polymer-DTB-lipid is typically included in a molar percentage of between about 1–20, more preferably between about 2–15 mole percent, and still more preferably between about 4–12 mole percent. In studies performed in support of the invention, described below, liposomes comprised of 60 mole percent neutral-cationic lipid and 5 mole percent of polymer-DTB-lipid.

Liposomes prepared in accordance with the invention can be sized to have substantially homogeneous sizes in a selected size range, typically between about 0.01 to 0.5 microns, more preferably between 0.03–0.40 microns. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin, F. J., in *Specialized Drug Delivery Systems-Manufacturing and Production Technology*, (P. Tyle, Ed.) Marcel Dekker, New York, pp. 267–316 (1990)).

B. Preparation and Characterization of Exemplary Compositions

In studies performed in support of the invention, a pNSL luciferase plasmic DNA with a CMV promoter was entrapped in liposomes comprised of the neutral-cationic lipid and the polymer-DTB-lipid. Targeting of the complexes was achieved by including either folate or FGF as targeting ligands. Typically, the targeting ligand was covalently attached to the distal end of the PEG chain in the polymer-DTB-lipid conjugate according to conventional chemistry techniques known in the art and described, for example, in U.S. Pat. No. 6,180,134.

Example 7 describes preparation of Formulation Nos. (7-1), (7-2), (7-3), (7-4, and (7-5) for administration to mice bearing Lewis lung carcinoma cell tumors. Formulation Nos. 2 and 3 included the neutral cationic lipid described above in FIG. 1 (Compound V) an the mPEG-DTB-lipid described in FIG. 4, where R was H (also referred to herein as "FC PEG" or "fast-cleavable PEG) The formulations also included an FGF targeting ligand. Formulations Nos. 1, 4 and 5 served as comparative controls.

The liposome-DNA complexes were administered intravenously to the test mice. Twenty four hours later, tumor and other tissues were collected and analyzed for luciferase expression. The results are shown in Table 1.

TABLE 1

Luciferase Expression in Lewis-lung carcinoma bearing mice after intravenous administration of FGF-targeted liposome formulations

| Formulation No. (See Example 7 for details) | Targeting Ligand | Luciferase Expression (pg luciferase/ag protein) | | |
|---|---|---|---|---|
| | | Tumor | Lung | Liver |
| Formulation No. 7-1 (HDSG/CHOL) | FGF | 15.3 | 1.4 | 1.2 |
| Formulation No. 7-2 (HDSG/CHOL/F-C PEG) | FGF | 7.8 | 1.9 | 4.5 |

TABLE 1-continued

Luciferase Expression in Lewis-lung carcinoma bearing mice after intravenous administration of FGF-targeted liposome formulations

| Formulation No. (See Example 7 for details) | Targeting Ligand | Luciferase Expression (pg luciferase/ag protein) | | |
|---|---|---|---|---|
| | | Tumor | Lung | Liver |
| Formulation No. 7-3 (HDSG/PHSPC/F-C PEG) | FGF | 1.2 | 2.0 | 3.2 |
| Formulation No. 7-4 (HDSG/PHS PC/PEG) | FGF | 3.7 | 2.0 | 4.6 |
| Formulation No. 7-5 (DDAB/CHOL) | folate | 4.3 | 403.9 | 25.4 |

The luciferase expression in the lung for the liposomes composed of DDAB (Formulation No. 5), which is a cationic liposome, is nearly 100-fold higher than the other formulations. This is due to the large surface area in the lung and the electrostatic charge interaction between the positively charged plasmid-liposome complexes and the negatively charged endothelial cell surfaces in the lung. The liposome composition in accord with the invention where the neutral-cationic lipid is used rather than a cationic lipid overcomes this problem. Formulations 1–4 all include the HDSG neutral-cationic lipid (Compound V of FIG. 1). Since the lipid is neutral at physiologic pH (7.4) the liposomes do not stick to the lung surfaces, allowing the liposomes to distribute systemically. This improved biodistribution is reflected in the higher luciferase expression in the tumor tissue for Formulations 1 and 2.

Examples 8–12 describe other studies performed in support of the invention, where FGF-targeted liposome/DNA complexes were administered to mice inoculated with Lewis lung tumors or to mice injected with Matrigel, an FGF-angiogenic endothelial cell model for tumor vasculature targeting. In these studies, liposomes in accord with the invention were composed of the neutral-cationic lipid HDSG (Compound V of FIG. 1) and either cholesterol or PHSPC. PEG-DTB-lipid was also included in the formulations in accord with the invention. A cationic lipid was also included in the complexes, to determine the effect of the cationic lipid on complex stability and transfection efficiency. Two cationic lipids were utilized, DOTAP and $N^2$—[$N^2,N^5$-bis(3-aminopropyl)-L-ormithyl]-N,N-dioctadecyl-L-glutamine tetrahydrotrifluoroacetate, referred to herein as "GC33".

The formulations were administered intravenously to the tumor-bearing or Matrigel-bearing mice and luciferase expression was measured in the Matrigel or tumor, the lung and the liver 24 hours after administration. In one study (Example 10) tumor cells and Matrigel were implanted in the same mouse on opposing flanks. The results are shown in Tables 2–6.

TABLE 2

| Formulation No. (See Example 8 for details) | Targeting Ligand | Luciferase Expression (pg luciferase/mg protein) | | |
|---|---|---|---|---|
| | | Matrigel | Lung | Liver |
| Formulation No. 8-1 (DOTAP/Chol) | none | 28.6 | 2286.1 | 18.1 |
| Formulation No. 8-2 (HDSG/PHSPC) | FGF | 16.0 | 126.7 | 3.1 |
| Formulation No. 8-3 (HDSG/PHSPC/FC-PEG) | FGF | 8.9 | 4.1 | 1.2 |
| Formulation No. 8-4 (HDSG/DOTAP/PHSPC) | none | 9.9 | 4.4 | 1.7 |
| Formulation No. 8-5 (HDSG/DOTAP/PHSPC) | FGF | 10.3 | 3.8 | 1.6 |
| Formulation No. 8-6 (HDSG/DOTAP/PHSPC/FC-PEG) | FGF | 14.2 | 2.0 | 1.3 |
| Formulation No. 8-7 (HDSG/GC33/PHSPC) | none | 10.5 | 223.1 | 2.7 |
| Formulation No. 8-8 (HDSG/GC33/PHSPC) | FGF | 11.2 | 121.3 | 3.1 |
| Formulation No. 8-9 (HDSG/GC33/PHSPC/FC-PEG) | FGF | 11.3 | 96.0 | 2.2 |

TABLE 3

| Formulation No. (See Example 9 for details) | Targeting Ligand | Luciferase Expression (pg luciferase/ mg protein) | |
|---|---|---|---|
| | | Tumor | Lung |
| Formulation No. 9-1 (DOTAP/Chol) | none | 3.4 | 18317.0 |
| Formulation No. 9-2 (HDSG/PHSPC) | FGF | 6.5 | 306.4 |
| Formulation No. 9-3 (HDSG/PHSPC/FC-PEG) | FGF | 5.6 | 2.8 |
| Formulation No. 9-4 (HDSG/DOTAP/PHSPC) | none | 4.4 | 9.7 |
| Formulation No. 9-5 (HDSG/DOTAP/PHSPC) | FGF | 17.1 | 7.4 |
| Formulation No. 9-6 (HDSG/DOTAP/PHSPC/FC-PEG) | FGF | 4.3 | 4.6 |
| Formulation No. 9-7 (HDSG/GC33/PHSPC) | none | 2.4 | 78.0 |
| Formulation No. 9-8 (HDSG/GC33/PHSPC) | FGF | 1.4 | 377.2 |
| Formulation No. 9-9 (HDSG/GC33/PHSPC/FC-PEG) | FGF | 2.1 | 42.1 |

TABLE 4

| Formulation No. (See Example 10 for details) | Targeting Ligand | Luciferase Expression (pg luciferase/mg protein) | | | |
|---|---|---|---|---|---|
| | | Tumor | Matridge 1 | Lung | Liver |
| Formulation No. 10-1 (DOTAP/Chol) | none | 16.8 | 13.6 | 38956.8 | 139.5 |
| Formulation No. 10-2 (HDSG/DOTAP/CHOL) | none | 37.1 | 27.8 | 91.7 | 2.3 |
| Formulation No. 10-3 (HDSG/DOTAP/CHOL) | FGF | 22.1 | 87.3 | 23.6 | 1.0 |
| Formulation No. 10-4 (HDSC/DOTAP/CHOL/FC-PEG) | FGF | 179.4 | 10.1 | 5.5 | 2.6 |
| Formulation No. 10-5 (HDSC/GC33/PHSPC) | none | 20.0 | 5.1 | 2.2 | 7.9 |
| Formulation No. 10-6 (HDSG/GC33/PHSPC) | FGF | 38.9 | 18.8 | 2.0 | 1.2 |
| Formulation No. 10-7 (HDSG/GC33/PHSPC/FC-PEG) | FGF | 16.7 | 4.3 | 2.1 | 2.2 |

TABLE 5

| Formulation No. (See Example 11 for details) | Targeting Ligand | Luciferase Expression (pg luciferase/mg protein) | | |
|---|---|---|---|---|
| | | Matrigel | Lung | Liver |
| Formulation No. 11-1 (DOTAP/Chol) | none | 35.0 | 102929.3 | 116.9 |
| Formulation No. 11-2 (HDSG/PHSPC) | FGF | 34.3 | 1.6 | 2.1 |
| Formulation No. 11-3 (HDSG/DOTAP/PHSPC) | FGF | 45.5 | 1.7 | 2.3 |
| Formulation No. 11-4 (HDSG/DOTAP/CHOL) | none | 40.9 | 62.0 | 3.0 |
| Formulation No. 11-5 (HDSG/DOTAP/CHOL) | FGF | 21.4 | 61.2 | 4.0 |
| Formulation No. 11-6 (HDSG/DOTAP/CHOL/FC-PEG) | FOF | 64.5 | 4.0 | 1.6 |
| Formulation No. 11-7 (HDSG/DOTAP/CHOL) | sialyl Lewis-X | 42.8 | 34.1 | 2.2 |
| Formulation No. 11-8 (HDSC/DOTAP/CHOL) | FGF | 38.1 | 12.4 | 2.6 |

TABLE 6

| Formulation No. (See Example 12 for details) | Targeting Ligand | Luciferase Expression (pg luciferase/mg protein)[1] | | |
|---|---|---|---|---|
| | | Tumor | Lung | Liver |
| Formulation No. 12-1 (DOTAP/Chol) | none | 72.1 | 273214.0 | 174.4 |
| Formulation No. 12-2 (HDSG/PHSPC) (>5 days) | FGF | 17.5 | 9.2 | 3.5 |
| Formulation No. 12-3 (HDSG/PHSPC) (1 day) | FGF | 32.8 | 8.4 | 3.9 |
| Formulation No. 12-4 (HDSG/DOTAP/Chol/FC-PEG) (>5 days) | none | 22.3 | 12.2 | 6.2 |
| Formulation No. 12-5 (HDSG/DOTAP/Chol/FC-PEG) (1 day) | FGF | 33.4 | 23.2 | 2.5 |

[1] expression was measured 24 hours after liposome admininstration of Formulation Nos. 12-1, 12-3 and 12-5, and five days after administration of Formulation Nos. 12-2 and 12-4.

The data in Tables 2–6 show that using the HDSG neutral-cationic lipid rather than a conventional cationic lipid achieved an extended biodistribution of the DNA-liposome complexes. This feature can be seen by comparing, for example, the luciferase expression in the lung and tumor for formulation Nos. 9-1 and 9-2. This enhanced biodistribution achieved when the neutral cationic lipid was included in the liposomes even when a cationic lipid was present in addition to the neutral-cationic lipid, as seen when the results for Formulation Nos. 10-1 and 10-2 are compared.

The effect of the FGF targeting ligand on in vivo gene expression can be seen by comparing Formulation Nos. 9-2 with 9-3 and Formulation Nos. 9-5 with 9-6 and Formulation Nos. 10-3 with 10-4. In these formulations, luciferase expression was higher, and sometimes significantly higher, when the complexes included the FGF targeting ligand.

A comparison of Formulation Nos. 9-7, 9-8, and 9-9 with Formulation Nos. 10-5, 10-6, and 10-7 show that reducing the amount of GC33 from 22.5 mole percent to 11.25 mole percent shifts the luciferase expression from the lung to the tumor or Matrigel. This shift of expression level is due to a reduction in surface charge of the liposome-DNA complexes, indicating that the absence of surface charge at physiological pH increases blood retention time and changes the tissue distribution of the complexes after systemic administration.

Examples 13–15 describe in vivo administration of various liposome formulations to mice bearing a KB tumor. In these studies, the complexes included a folate ligand for targeting to the folate-expressing tumor cells. The formulations are described in Example 13–15 and the luciferase expression in the tumor lung and liver following intravenous administration are shown in Table 7–9.

TABLE 7

| Formulation No. (See Example 13 for details) | Targeting Ligand | Luciferase Expression (pg luciferase/ mg protein) | | |
|---|---|---|---|---|
| | | Tumor | Lung | Liver |
| Formulation No. 13-1 (DOTAP/Chol) | none | 4.2 | 16727.2 | 13.3 |
| Formulation No. 13-2 (HDSG/PHSPC) | folate | 4.2 | 2.5 | 1.0 |
| Formulation No. 13-3 (HDSG/PHSPC/FC-PEG) | folate | 7.3 | 2.4 | 1.0 |
| Formulation No. 13-4 (HDSG/DOTAP/PHSPC) | folate | 1.0 | 3.3 | 1.0 |
| Formulation No. 13-5 | folate | 10.5 | 2.7 | 1.1 |

TABLE 7-continued

| Formulation No. (See Example 13 for details) | Targeting Ligand | Luciferase Expression (pg luciferase/ mg protein) | | |
|---|---|---|---|---|
| | | Tumor | Lung | Liver |
| (HDSG/DOTAP/PHSPC/FC-PEG) | | | | |
| Formulation No. 13-6 (HDSG/GC33/PHSBC) | folate | 6.0 | 32.9 | 0.7 |
| Formulation No. 13-7 (HDSG/GC33/PHSPC/SC-PEG) | folate | 4.8 | 5.0 | 1.0 |
| Formulation No. 13-8 (HDSG/GC33/PHSPC/FC-PEG) | folate | 2.8 | 13.3 | 1.1 |

TABLE 8

| Formulation No. (See Example 14 for details) | Targeting Ligand | Luciferase Expression (pg luciferase/ mg protein) | | |
|---|---|---|---|---|
| | | Tumor | Lung | Liver |
| Formulation No. 14-1 (DOTAP/Chol) | none | 5.9 | 481.4 | 1.9 |
| Formulation No. 14-2 (HDSG/DOTAP/Chol) | folate | 3.3 | 2.2 | 1.6 |
| Formulation No. 14-3 (HDSG/DOTAP/Chol/FC-PEG) | folate | 3.6 | 7.6 | 1.2 |
| Formulation No. 14-4 (HDSG/DOTAP/Chol) | folate | 1.2 | 3.3 | 1.2 |
| Formulation No. 14-5 (HDSG/DOTAP/Chol/FC-PEG) | folate | 2.5 | 4.4 | 1.1 |

TABLE 9

| Formulation No. (See Example 13 for details) | Targeting Ligand | Luciferase Expression (pg luciferase/ mg protein) | | |
|---|---|---|---|---|
| | | Tumor | Lung | Liver |
| Formulation No. 15-1 (DOTAP/Chol) | none | 6.9 | 11575.7 | 10.5 |
| Formulation No. 15-2 (HDSG/PHSPC) | folate | 6.2 | 2.2 | 0.9 |
| Formulation No. 15-3 (HDSC/PHSPC/FC-PEG) | folate | 2.9 | 1.9 | 0.9 |
| Formulation No. 15-4 (HDSG/DOTAP/PHSPC) | folate | 0.3 | 2.2 | 1.0 |
| Formulation No. 15-5 (HDSG/DOTAP/PHSPC/FC-PEG) | folate | 0.8 | 2.0 | 1.3 |
| Formulation No. 15-6 (HDSG/DOTAP/Chol) | folate | 2.0 | 17.0 | 1.1 |
| Formulation No. 15-7 (HDSG/DOTAP/Chol/FC-PEG) | folate | 2.4 | 3.0 | 2.1 |

Tables 7–9 show that inclusion of the neutral-cationic lipid alters the biodistribution compared to that observed for liposomes prepared with cationic lipids (Formulation Nos. 13-1, 14-1, 15-1). The highest transfection was observed for Formulation No. 13-5, which is of liposomes comprised of the neutral-cationic lipid, the PEG-DTB-lipid and a folate targeting ligand.

VI. EXAMPLES

The following examples illustrate but in no way are intended to limit the invention.

Materials: The following materials were obtained from the indicated source: partially hydrogenated soy phosphatidylcholine (Vernon Walden Inc., Green Village, N.J.); cholesterol (Solvay Pharmaceuticals, The Netherlands); dioleoylphosphatidyl ethanolamine (DOPE) and dimethyldioctadecylammonium (DDAB) (Avanti Polar Lipids, Inc., Birmingham, Ala.).

Methods Dynamic light scattering was performed using a Coulter N4-MD (Coulter, Miami Fla.).

Zeta-Potential: Zeta potential was measured using a ZETASIZER 2000 from Malver Instruments, Inc. (Southborough, Mass.). The instrument was operated as follows: number of measurements: 3; delay between measurements: 5 seconds; temperature: 25 C.; viscosity: 0.89 cP; dielectric constant: 79; cell type: capillary flow; zeta limits: −150 mV to 150 mV.

Example 1

Preparation of Exemplary Neutral-Cationic Lipid

A. Preparation of para-nitrophenyl carbonate of distearoyl glycerol

As illustrated in FIG. 1, 1,2-distearoyl-sn-glycerol (500 mg, 0.8 mmol; Compound I) was dried azeotropically with benzene (3 times with rotary evaporator). Para-nitrophenyl chloroformate (242 mg, 1.2 mmol, 1.5 eq; Compound II), 4-dimethylaminopyridine (10 mg, 0.08 mmol,0.1 eq), and triethylamine (334 µl, 204 mmol, 3 eq) were added to 1,2-distaroyl glycerol in $CHCl_3$(5 ml). The reaction mixture was stirred at room temp for 2 h. TLC showed that the reaction was complete. The mixture was diluted with $CHCl_3$ (50 ml) and extracted with 10% citric acid (3×15 mL) The organic layer was dried ($MgSO_4$) and evaporated to give a solid. The solid (light orange) was washed with acetonitrile (4×3 mL) to remove excess of p-nitrophenyl chloroformate. The product, para-nitrophenyl carbonate of distearoyl glycerol (Compound III), was dried under vacuum over $P_2O_5$. Yield: 557 mg (88%). $^1H$ NMR (360 MHz, DMSO-D6,): δ 0.88 (t, $CH_3$, 6H); 1.26 (s, $CH_2$ 58H); 1.62 (m, $CH_2CH_2CO$, 4H); 2.4 (2xt, $CH_2CO$, 4H); 4.2 (dd, trans $CH_2OCO$, 1H); 4.35 (m, $CH_2OCOO$, 2H); 4.5 (dd, cis $CH_2OCO$, 1H); 5.38 (m, $CH_2CHCH_2$, 1H); 7.4 (d, $C_6H_5$, 2H); 8.3 (d, $C_6H_5$, 2H).

B. Preparation of Carbamate of Histamine and Distearoyl Glycerol

Para-nitrophenyl carbonate of 1,2-distearoyl glycerol (350 mg, 0.44 mmol, Compound III) was added to Histamine (46 mg, 0.40 mmol, 0.9 eq; Compound IV) in $CHCl_3$ (1 ml) with DMSO (200 µl). Pyridine (300 µl; Compound V) was added to the solution. The reaction mixture was stirred at room temperature overnight (~20 h). TLC ($CHCl_3$:MeOH=90:10) showed that the reaction was complete. Solvent was evaporated. The product (Compound VI) was dissolved in $CHCl_3$, poured on to silica gel (Aldrich, 230–400 mesh, 60 Å) column, and eluted with following solvents, $CHCl_3:CH_3COCH_3$=90:10, 40 ml (upper spot eluted); $CHCl_3$:IPA=80:20, 40 ml (product eluted); $CHCl_3$:IPA=70:30, 40 ml (more product eluted). Fractions containing pure product were combined, and evaporated. The product was dried under vacuo over $P_2O_5$ and was obtained as white solid (236 mg, 80% yield). $^1H$ NMR (360 MHZ, $CDCl_3$/MeOH=1:1 with TMS): δ 0.88 (t, CH3, 6H.); 1.28 (s, $CH_2$, 56H; 1.62 (m, $CH_2CH_2CO$, 4H); 2.34 (2xt, $CH_2CO$, 4H); 2.77 (t, $CH_2CH_2NH$, 2H); 3.18 (t, $CH_2CH_2CO$, 2H); 4.05–4.2 (dd, cis and trans $CH_2CHCH_2$, 4H); 5.13 (m, $CH_2CHCH_2$, 1H); 608 (s, Histamine, 1H); 7.53 (s, Histamine, 1H).

Example 2

Synthesis of mPEG-DTB-DSPE

The reaction scheme is illustrated in FIG. 4.

mPEG-MeDTB-nitrophenylcarbonate (300 mg, 0.12 mmol, 1.29 eq) was dissolved in $CHCl_3$ (3 ml). DSPE (70 mg, 0.093 mol) and TEA (58.5 µl, 0.42 mmol, 4.5 eq) were added to PEG-solution, and was stirred at 50° C. (oil bath temp). After 15 minutes, TLC showed that the reaction didn't go to completion. Then two portions of TEA (10 µl, and 20 µl), and few portions of mPEG-MeDTB-nitrophenylcarbonate (50 mg, 30 mg, 10 mg) were added every after 10 minutes, until the reaction went to completion. Solvent was evaporated. Product mixture was dissolved in MeOH, and 1 g of C8 silica was added. Solvent was evaporated again. Product containing C8 silica was added on the top of the column, and was eluted with $MeOH:H_2O$ gradient (pressure), $MeOH:H_2O=30:70$, 60 ml; $MeOH:H_2O=50:50$, 60 ml; $MeOH:H_2O=70:30$, 140 ml (starting material eluted); $MeOH:H_2O=75:25=40$ ml; $MeOH:H_2O=80:20$, 80 ml (product eluted); $MeOH:H_2O=85:15$, 40 ml; $MeOH:H_2O=90:10$, 40 ml; MeOH=40 ml; $CHCl_3:MeOH:H_2O=90:18:10$, 40 ml. Fractions containing pure product were combined and evaporated to give product as colorless thick liquid. Tertiary butanol (5 ml) was added to it, lyophilized and the dried in vacuo over $P_2O_5$ to give product as white fluffy solid (252 mg, 89% yield).

The ortho- and para-DTB-DSPE compounds were purified by silica gel chromatography (methanol gradient 0–10% in chloroform, ≈70% isolated yield) and the structures confirmed by NMR and MALDI-TOFMS. ($^1$H NMR for para conjugate: (d6-DMSO, 360 MHz) δ 0.86 (t, $CH_3$, 6H), 1.22 (s, $CH_2$ of lipid, 56H), 1.57 (m, $CH_2CH_2CO_2$, 4H), 2.50 (2×t, $CH_2CO_2$, 4H), 2.82 (t, $CH_2S$, 2H), 3.32 (s, $OCH_3$, 3H), 3.51 (m, PEG, ≈180 H), 4.07 (t, $PEG-CH_2OCONH$, 2H), 4.11 & 4.28 (2×dd $CH_2CH$ of glycerol, 2H), 4.98 (s, benzyl-$CH_2$, 2H), 5.09 (m, $CHCH_2$ of lipid), 7.35 & 7.53 (2×d, aromatic, 4H) ppm. The ortho conjugate differed only in benzyl and aromatic signals at 5.11 (s, $CH_2$, 2H), and 7.31 (d, 1H), 7.39 (m, 2H) 7.75(d, 1H) ppm.

MALDI-TOFMS produced a distribution of ions spaced at equal 44 Da intervals, corresponding to the ethylene oxide repeating units. The average molecular weights of the compounds was 3127 and 3139 Da for para and ortho isomers respectively (theoretical molecular weight ≈3100 Da).

Example 3

Synthesis of mPEG-DTB-DSPE

A. mPEG-MeDTB-DSPE

This reaction scheme is illustrated in FIGS. 6A–6B.

mPEG(5K)-OH (40 g, 8 mmol) was dried azeotropically with toluene (total volume was 270 ml, 250 ml was distilled off by Dean-Stark). Dichloromethane (100 ml) was added to mPEG-OH. P-nitrophenyl chloroformate (2.42 g, 12 mmol, 1.5 eq), and TEA (3.3 ml, 24 mmol, 3 eq) were added to PEG solution at 4° C. (ice water), while taking precautions against moisture. Light yellow TEA hydrochloride salt was formed. After 15 minutes cooling bath was removed, and the reaction mixture was stirred at room temperature overnight. TLC showed ($CHCl_3:MeOH:H_2O=90:18:2$) that the reaction was complete. Solvent was evaporated. The residue was dissolved in ethyl acetate (~50° C.). TEA hydrochloride salt was filtered off and washed with warm ethyl acetate. Solvent was evaporated and the product recrystallized with isopropanol (three times). Yield: 38.2 g (92%). $^1$H NMR (DMSO-$d_6$, 360 MHz) δ 3.55 (s, PEG, 450H); 4.37 (t, $PEG-CH_2$, 2H); 7.55 (d, $C_6H_5$, 2H); 8.31 (d, $C_6H_5$, 2H).

1-Amino-2-propanol (1.1 ml, 14.52 mmol, 3 eq), and TEA (2.02 ml, 14.52 mmol, 3 eq) were added to mPEG (5K)-nitrophenyl carbonate (25 g, 4.84 mmol) in DMF (60 ml) and $CH_2Cl_2$ (40 ml). It was a yellow clear solution. The reaction mixture was stirred at room temperature for 30 minutes. TLC ($CHCl_3:MeOH=90:10$) showed that the reaction went to completion. Solvent (dichloromethane) was evaporated. Isopropanol (250 ml) was added to the product mixture in DMF (60 ml). Product precipitated immediately, and then recrystallized with iPrOH (three times).

Yield: 22.12 g (90%). $^1$H NMR (DMSO-$d_6$, 360 MHz) δ 0.98 (d, $CH_3CH(OH)CH_2$, 3H); 3.50 (s, PEG, 180H); 4.03 (t, $PEG-CH_2$, 2H); 4.50 (d, $CH_3CHOH$, 1H); 7.0 (t, mPEG-OCONH).

mPEG(5K)-urethane-2-methyl propanol (22.12 g, 4.34 mmol) was dried azeotropically with toluene (45 ml). Dichloromethane (60 ml) was added to it. Methane sulfonyl chloride (604.6 µl, 7.81 mmol, 1.8 eq) and TEA (3.93 ml, 28.21 mmol, 6.5 eq) were added to mPEG-solution at 0° C. while maintaining stirring and taking precautions against moisture. After 30 minutes, cooling bath was removed, and the reaction mixture was stirred at room temperature for 16 h. Solvent was evaporated. Ethyl acetate was added to remove TEA salts. The product was recrystallized with isopropanol (three times). Yield: 20.27 g (90%). $^1$H NMR (DMSO-$d_6$, 360 MHz) δ 1.27 (d, $CH_3CHOSO_2CH_3$, 3H); 3.162 (s, $CH_3O_2SOCH$, 3H); 3.50 (s, PEG, 180H); 4.07 (t, $PEG-CH_2$, 2H); 4.64 (q, $CH_3CHOH$, 1H); 7.43 (t, mPEG-OCONH).

mPEG(5K)-urethane-2methyl-methane sulfone (10.27 g, 1.98 mmol) was dried azeotropically with toluene (20 ml, each time). Sodium hydride (377 mg, 9.4 mmol, 4.75 eq) was added in anhydrous toluene (60 ml) at 0° C. (in ice water). After 5 minutes, triphenylmethanethiol (3.92 g, 14.6 mmol, 7.15 eq) was added to the solution. After 10 minutes, mPEG-urethane-2methyl-methane sulfone (10.27 gm, 1.98 mmol) was added to the reaction mixture. It became a yellow solution. After 45 minutes, TLC ($CHCl_3:MeOH:H_2O=90:18:2$) showed that the reaction went to completion. Acetic acid (445.57 µl, 7.42 mmol, 3.75 eq) was added to the reaction mixture to neutralize excess of sodium hydride. The solution became thick and whitish. Solvent was evaporated and the solid was recrystallized with ethyl acetate (30 ml) and isopropanol (70 ml). The product mixture did not dissolve completely, while precipitate filtered off. Then the product mixture was recrystallized with isopropanol/tert-butyl alcohol (100 ml/20 ml). Yield: 8.87 g (84%). $^1$H NMR (DMSO-$d_6$, 360 MHz) δ 0.74 (d, $CH_3CHSC(C_6H_5)_3$, 3H), 3.50 (s, PEG, 180H), 4.0 (t, $PEG-CH_2$, 2H), 4.64 (q, $CH_3CHOH$, 1H); 7.49 (t, mPEG-OCONH); 7.20–7.41 (m, $SC(C_6H_5)_3$, 15H).

mPEG(5K)-urethane-2methyl-triphenylmethanethiol (8.87 g, 1.65 mmol) was dissolved in $TFA/CH_2Cl_2$ (10 ml/10 ml) at 0° C. Under vigorous stirring, methoxy carbonylsulfenyl chloride (185.5 µl, 1.99 mmol, 1.2 eq) was added to the solution. The reaction mixture was stirred at room temperature for 15 minutes. TLC ($CHCl_3:MeOH=90:10$) showed that the reaction was complete. Solvents were evaporated. The product mixture was recrystallized with isopropanol:tert-butyl alcohol (80 ml:20 ml) two times. Tertiary butanol (5 ml) was added to the product, which was then lyophilized and dried in vacuo over $P_2O_5$ to give product as white fluffy solid (8.32 g, 97% yield). $^1$H NMR (DMSO-$d_6$, 360 MHz) δ 1.17 (d, $CH_3CHSSCOOCH_3$, 3H);

3.42 (s, PEG, 180H); 3.84 (s, CH$_3$OCOSSCH, 3H); 4.05 (t, mPEG-CH$_2$, 2H); 7.38 (t, mPEG-OCONH, 1H).

mPEG(5K)-urethane ethyl(methyl)dithiocarbonyl methoxide (8.32 g, 1.6 mmol) was dissolved in dry methanol (20 ml), and chloroform (2.5 ml). A solution of mercapto benzyl alcohol (592 mg, 4 mmol, 2.5 eq) in dry methanol (2 ml) was added to the PEG-solution. The reaction mixture was stirred at room temperature for 18 h. Solvent was evaporated, product mixture was recrystallized with ethyl acetate/isopropanol, 30 ml/100 ml (3 times). NMR showed ~16% product was formed. So, another portion of mercapto benzyl alcohol (322 mg, 2.18 mmol, 1.8 eq) in MeOH (2 ml) was added dropwise to the product mixture in MeOH/CHCl$_3$ (24 ml/1 ml) at 0° C. (ice water). After addition (~10 minutes) completion, ice bath was removed, and the reaction mixture was stirred at room temperature for 24 h. TLC (CHCl$_3$:MeOH:H$_2$O=90:18:2) showed that the reaction was complete. Solvent was evaporated, and then product mixture was recrystallized with ethyl acetate/isopropanol, 30 ml/100 ml. Yield: 7.25 g, (94%).

$^1$H NMR (DMSO-d$_6$, 360 MHz) δ 1.56 (d, CH$_3$CHSSC$_6$H$_5$CH$_2$OH, 3H); 3.29 (CH$_3$O-PEG, 3H); 3.50 (s, PEG, 450H); 4.03 (t, mPEG-CH$_2$, 2H); 4.46 (d, HOCH$_2$C$_6$H$_5$, 2H); 5.16 (t, HOCH$_2$C$_6$H$_5$, 1H); 7.30 (d, C$_6$H$_5$, 2H); 7.40 (br t, mPEG-OCONH, 1H); 7.50 (d, C$_6$H$_5$, 2H).

mPEG(5K)-urethane-ethyl (methyl)-dithiobenzyl alcohol (6.75 g, 1.27 mmol) was dissolved in CHCl$_3$ (30 ml), P-nitrophenyl chloroformate (513 mg, 2.54 mmol, 2 eq) was added to it at 0° C. (ice water). After 5 minutes triethylamine (531 µl, 3.81 mmol, 3 eq) was added. After 30 minutes ice bath was removed, and the reaction mixture was stirred at room temperature overnight. Solvent was evaporated. The product mixture was dissolved in ethyl acetate. TEA salt was filtered off, and then solvent was evaporated. Then the product mixture was recrystallized with ethyl acetate/isopropanol, 30 ml/100 ml (three times). Yield: 6.55 g (94%). $^1$H NMR (DMSO-d$_6$, 360 MHz) δ 1.17 (d, CH$_3$CHSSC$_6$H$_5$, 3H); 3.24 (CH$_3$O-PEG, 3H); 3.40 (s, PEG, 180H); 4.03 (br t, mPEG-CH$_2$, 2H); 5.28 (S, C$_6$H$_5$CH$_2$OCO, 2H); 7.45–8.35 (m, C$_6$H$_5$)$_2$, 8H)

mPEG-MeDTB-nitrophenylcarbonate (766 mg, 0.14 mmol, 1.29 eq) was dissolved in CHCl$_3$ (5 ml). DSPE (70 mg, 0.093 mol) and TEA (58.5 µl, 0.42 mmol, 4.5 eq) were added to PEG-solution, and was stirred at 50° C. (oil bath temp). After 20 minutes, TLC showed that the reaction didn't go to completion. More mPEG-MeDTB-nitrophenylcarbonate (total 1239 mg, 0.23 mmol, 2.47 eq) and 1-hydroxybenztriazole (HOBt) (25 mg, 0.19 mmol, 2 eq) were added. After 20 minutes, TLC (CHCl$_3$:MeOH:H$_2$O=90:18:2, with molybdenum and ninhydrin) showed that the reaction was complete. Solvent was evaporated. Product mixture was dissolved in warm (42° C.) ethyl acetate. It was a cloudy solution (TEA salt precipitated). The solution was filtered, and solvent was evaporated. MeOH, and 2 g of C8 silica was added to the product mixture. Solvent was evaporated again. Product containing C8 silica was added on the top of the column, and was eluted with MeOH:H$_2$O gradient (pressure), MeOH:H$_2$O30:70, 100 ml; MeOH H$_2$O 50:50, 100 ml; MeOH H$_2$O 70:30, 250 ml (starting material eluted); MeOH H$_2$O 75:25=40 ml; MeOH H$_2$O 80:20, 200 ml (product eluted); MeOH=100 ml; CHCl$_3$:MeOH:H$_2$O=90:18:2, 100 ml; CHCl$_3$:MeOH H$_2$O=75:36:6, 100 ml. Fractions containing pure product were combined and evaporated to give product as colorless thick liquid. Tertiary butanol (5 ml) was added to it, lyophilized and then dried in vacuo over P$_2$O$_5$ to give product as white fluffy solid (467 mg, 83% yield). $^1$H NMR (DMSO-d$_6$, 360 MHz) δ 0.83 (d, 2(CH$_3$), 3H); 1.16 (d, CH$_3$CHSSC$_6$H$_5$, 3H); 1.21 (s, 28(CH$_2$, 56H); 1.47 (br m, CH$_2$CH$_2$CO, 4H); 2.23 (2×t, CH$_2$CH$_2$CO, 4H); 3.50 (s, PEG, 180H); 4.04 (br t, mPEG-CH$_2$, 2H); 4.05 (trans d, PO$_4$CH$_2$CHCH$_2$, 1H); 4.24 (cis d, PO$_4$CH$_2$CHCH$_2$, 1H); 4.97 (s, C$_6$H$_5$CH$_2$OCO-DSPE, 2H); 5.03 (br s, (PO$_4$CH$_2$CH, 1H); 7.32 (d, C$_6$H$_5$, 2H); 7.53 (d, C$_6$H$_5$, 2H); 7.52 (br s, mPEG-OCONH, 1H). MALDI-TOFMS produced a bell shaped distribution of ions spaced at equal 44 Da intervals, corresponding to the ethylene oxide repeating units. The average molecular mass of the conjugate and mPEG-thiol (mostly cleaved disulfide) is 6376 and 5368 Da (theoretical molecular mass ~6053, and 5305 Daltons).

B. mPEG-ethylDTB-DSPE mPEG-urethane ethyl(ethyl)dithiocarbonyl methoxide (2 g, 0.90 mmol) was dissolved in dry methanol (8 ml). At the beginning the solution was cloudy, but after 5 minutes it became a clear solution. Mercaptobenzyl alcohol (265.2 mg, 1.79 mmol, 2 eq) was added to the PEG-solution. The reaction mixture was stirred at room temperature for 30 hours. Ether (70 ml) was added to the reaction solution to precipitate the product, and kept at 4° C. overnight. The white solid was filtered and recrystallized with ethyl acetate/ether, 30 ml/70 ml. Yield: 1.96 g, (94%). $^1$H NMR (DMSO-d$_6$, 360 MHz) δ 0.86 (d, CH$_3$CH$_2$CHSSC$_6$H$_5$CH$_2$OH, 3H); 1.42 (p, CH$_3$CH$_2$CHSSC$_6$H$_5$CH$_2$OH, 1H); 1.64 (p, CH$_3$CH$_2$CHSSC$_6$H$_5$CH$_2$OH, 1H); 3.51 (s, PEG, 180H); 4.03 (t, mPEG-CH$_2$, 2H); 4.47 (d, HOCH$_2$C$_6$H$_5$, 2H); 5.20 (t, HOCH$_2$C$_6$H$_5$, 1H); 7.31 (d, C$_6$H$_5$, 2H); 7.42 (br t, mPEG-OCONH, 1H); 7.49 (d, C$_6$H$_5$, 2H).

N-hydroxy-s-norbornene-2,3-dicarboxylic acid imide (HONB) (48 mg, 0.269 mmol) was added to DSPE (55 mg, 0.073 mmol) in CHCl$_3$ (3 ml) at 50° C. (oil bath temperature). After 3–4 minutes it became a clear solution. Then mPEG-EtDTB-nitrophenylchloroformate (334 mg, 0.134 mmol) was added, followed by triethylamine (TEA, 45 µl, 0.329 mmol). After 20 minutes TLC (CHCl$_3$:MeOH:H$_2$O=90:18:2) showed that the reaction went to completion (molybdenum and ninhydrin sprays). Solvent was evaporated. Product mixture was dissolved in methanol, mixed with C8 silica (1 g) and striped of the solvent by rotary evaporation. The solid residue was added on the top of the C8-column, which was then eluted with MeOH:H$_2$O gradient (pressure), MeOH:H$_2$O=30:70, 60 ml; MeOH:H$_2$O=50:50, 60 ml; MeOH:H$_2$O=70:30, 140 ml; MeOH:H$_2$O=75:25 =140 ml (starting material eluted); MeOH:H$_2$O=80:20, 80 ml; MeOH:H$_2$O=90:10, 140 ml (product eluted); MeOH=40 ml; CHCl$_3$:MeOH:H$_2$O=90:18 10, 40 ml. Fractions containing pure product were combined and evaporated to give product as colorless thick liquid. Tertiary butanol (5 ml) was added, lyophilized and then dried in vacuo over P$_2$O$_5$ to give product as white fluffy solid (175 mg, 78% yield). $^1$H NMR (DMSO-d$_6$, 360 MHz) δ 0.85 (d, 2(CH$_3$), 6H; d, CH$_3$CHSSC$_6$H$_5$, 3H); 1.22 (s, 28(CH$_2$), 56H); 1.49 (br m, CH$_2$CH$_2$CO, 4H); 2.24 (2×t, CH$_2$CH$_2$CO, 4H); 3.50 (s, PEG, 180H); 4.04 (br t, mPEG-CH$_2$, 2H); 4.08 (trans d, PO$_4$CH$_2$CHCH$_2$, 1H); 4.27 (cis d, PO$_4$CH$_2$CHCH$_2$, 1H); 4.98 (s, C$_6$H$_5$CH$_2$OCO-DSPE, 2H); 5.06 (br s, (PO$_4$CH$_2$CH, 1H); 7.34 (d, C$_6$H$_5$, 2H); 7.53 (d, C$_6$H$_5$, 2H); 7.55 (br s, mPEG-OCONH, 1H).

Example 4

Synthesis of mPEG-DTB-nitrophenylchloroformate

This reaction scheme is illustrated in FIG. 7.

A. Procedures for Synthesis of 1-(mercaptomethyl) Ethylammonium Chloride 1. 2-Amino-1-methylethyl hydrogen sulfate. 1-Amino-2-propanol (22.53 g, 0.3 mol) was vigorously stirred in an ice bath. Sulfuric acid (16.10 ml, 0.3 mol) was added very slowly, over the course of one hour. Thick vapors and a very viscous solution were formed in the flask. After addition was complete, the reaction was heated between 170° C. and 180° C., under reduced pressure, connected to the house vacuum. Upon heating, the reaction turned light brown. After all water was removed (approximately 1 hour) it was allowed to cool to room temperature. Upon cooling a brown, glassy solid was formed which would crystallize when triturated with methanol. It was dissolved in water (50 ml) at 60° C. Enough warm methanol was added to make the solution 80% methanol. Upon cooling, crystals formed which were then filtered and dried over $P_2O_5$. Yield: 17.17 g (37%). $^1$H NMR ($D_6$-DMSO): δ 1.16 (d, $CH_3$, 3H); δ 2.78 (dd, $NH_3$—$CH_2$, 1H); δ 2.97 (dd, $NH_3$—$CH_2$, 1H); δ 4.41 (m, CH—$OSO_3$, 1H); δ 7.69 (s, $H_3N$, 3H). Melting point: 248°–250° C. (lit: 250° C.)

2. 5-Methylthiazolidine-2-thione. 2-Amino-1-methylethyl hydrogen sulfate (23.03 g, 148 mmol) and carbon disulfide (10.71 ml, 178 mmol, 1.2 eq.) were stirred in a 250 ml round-bottom-flask in 50% aqueous ethanol (40 ml). To this, sodium hydroxide (13.06 g, 327 mmol, 2.2 eq.) in 50% aqueous ethanol (50 ml) was added drop-wise, very slowly. Upon addition of sodium hydroxide, all starting materials dissolved and the solution turned orange. The reaction was refluxed (85° C.) for 40 minutes, after which time it turned bright yellow and a thick precipitate was formed. Ethanol was evaporated and then the aqueous solution was warmed and then filtered through a Buchner funnel to remove all water-soluble impurities. The remaining crystals were dissolved in warm ethanol and then warm water was added until the solution was 80% water. The mixture was allowed to cool and then refrigerated, yielding long, needle-like crystals. Yield: 14.64 g (75%). $^1$H NMR ($D_6$-DMSO): δ 1.33 (d, $CH_3$, 3H); δ 3.50 (m, $R_3CH$, 1H); δ 3.95 (dd, N—$CH_2$, 1H); δ 4.05 (m, N—$CH_2$, 1H); δ 10.05 (s, NH, 1H). Melting point: 92.5–93.5 (lit: 94–95).

3. 1-(mercaptomethyl)ethylammonium chloride. 5-Methylthiazolidine-2-thione (6.5 g, 49 mmol) was placed in a 250 ml round-bottom-flask. A solution of aqueous hydrochloric acid (40 ml, 18% in $H_2O$) was added and the flask was heated in an oil bath. The reaction refluxed (120° C.) for one week. Three times throughout the week 1 ml of concentrated hydrochloric acid was added. The reaction was monitored using TLC with ethyl acetate as eluent. They were visualized using UV, ninhydrin, and iodine vapors. Through most of the week the reaction was a heterogeneous mixture, with the starting material as oil which was denser than water. After one week the oil starting material was gone, although still visible on TLC. The reaction was removed from heat and allowed to cool to room temperature, and then was refrigerated to crystallize starting material. The crystallized starting material was filtered. Filtrate was evaporated and it was dried over $P_2O_5$ and NaOH to remove all water and HCl. The crude product was washed with two portions of diethyl ether (50 ml each) to remove all starting material. It was again dried over $P_2O_5$. Yield: 2.83 g (45%). $^1$H NMR ($D_6$-DMSO): δ 1.33 (d, $CH_3$, 3H); δ 2.92 (m, N—$CH_2$, 2H); δ 3.12 (m, SH, 1H); δ 3.18 (m, $R_3$—CH, 1H); δ 8.23 (bs, $NH_3$, 3H). Melting point: 80–82° C. (lit: 92–94).

B. Synthesis of mPEG-ethyl-DTB-nitrophenylchloroformate 1. 2-Amino-1-ethylethyl hydrogen sulfate. 1-Amino-2-butanol (15 ml, 158 mmol) was vigorously stirred in a 100 ml round-bottom-flask in an ice bath. Sulfuric acid (8.43 ml, 158 mmol) was added very slowly, over the course of one hour. Thick vapors and a very viscous solution were formed in the flask. After addition was complete, the reaction was heated between 170° and 180° C., under reduced pressure, connected to the house vacuum. Upon heating, the reaction turned light brown. After all water was removed (approximately 1 hour) it was allowed to cool to room temperature. Upon cooling a brown, glassy solid was formed. It was dissolved in hot water (50 ml) and then placed in the refrigerator overnight. Upon cooling, crystals formed which were then filtered and dried over $P_2O_5$. Yield: 9.98 g (37%). $^1$H NMR ($D_6$-DMSO): δ 0.87 (t, $CH_3$, 3H); δ 1.51 (q, $CH_3$—$CH_2$, 2H); δ 2.82 (dd, $NH_3$—$CH_2$, 1H); δ 3.00 (dd, $NH_3$—$CH_2$, 1H); δ 4.21 (m, CH—$OSO_3$, 1H); δ 7.70 (s, $H_3N$, 3H).

2. 5-Ethylthiazolidine-2-thione. 2-Amino-1-ethyl-ethyl hydrogen sulfate (9.98 g, 59 mmol) and carbon disulfide (4.26 ml, 71 mmol, 1.2 eq.) were stirred in a 100 ml round-bottom-flask in 50% aqueous ethanol (15 ml). To this, sodium hydroxide (5.20 g, 130 mmol, 2.2 eq.) in 50% aqueous ethanol (20 ml) was added drop-wise, very slowly. Upon addition of sodium hydroxide, all starting materials dissolved and the solution turned orange. The reaction was refluxed (85° C.) for 40 minutes, after which time it turned bright yellow and a thick precipitate was formed. Ethanol was evaporated and then the aqueous solution was warmed and then filtered through a Buchner funnel to remove all water-soluble impurities. The remaining crystals were dissolved in warm ethanol and then warm water was added until the solution was 80% water. The mixture was allowed to cool and then refrigerated, yielding needle-like crystals. Yield: 7.28 g (86%). $^1$H NMR ($D_6$-DMSO): δ 0.88 (t, $CH_3$, 3H); δ 1.66 (in, $CH_3$—$CH_2$, 2H); δ 3.58 (m, $R_3CH$, 1H); δ 3.93 (m, N—$CH_2$, 2H); δ 10.06 (s, NH, 1H). Melting point: 76–78° (lit: 76.6–76.9).

3. 1-(mercaptoethyl)ethylammonium chloride. 5-Ethylthiazolidine-2-thione (7.24 g, 50 mmol) was placed in a 250 ml round-bottom-flask. A solution of aqueous hydrochloric acid (45 ml, 18% in $H_2O$) was added and the flask was heated in an oil bath. Upon heating, the starting material melted, forming, all heterogeneous mixture. The reaction refluxed (120° C.) for one week. Four times throughout the week 1 ml of concentrated hydrochloric acid was added. The reaction was monitored using TLC with ethyl acetate as eluent. They were visualized using UV, ninhydrin, and iodine vapors. Throughout the week the reaction was a heterogeneous mixture, with the starting material as oil which was denser than water. The reaction was removed from heat and allowed to cool to room temperature, and then was refrigerated to crystallize starting material. The crystallized starting material was filtered. Filtrate was evaporated and it was dried over $P_2O_5$ and NaOH to remove all water and HCl. The crude product was washed with two portions of diethyl ether (50 ml each) to remove all starting material. It was again dried over $P_2O_5$. Yield: 3.66 g (52%). $^1$H NMR ($D_6$-DMSO):

Example 5

Synthesis of mPEG-DTB-lipid

This reaction scheme is illustrated in FIG. 8A.

1,2-distereoyl-sn-glycerol (500 mg, 0.8 mmol) was dried azeotropically with benzene (3 times). Para-nitrophenyl chloroformate (242 mg, 1.2 mmol, 1.5 eq), dimethylaminopyridine (DMAP) (10 mg, 0.08 mmol, 0.1 eq), and TEA (334.5 µl, 2.4 mmol, 3 eq) were added to 1,2-distereoyl glycerol in $CHCl_3$ (5 ml). The reaction mixture was stirred at room temperature for 2 h. TLC (Toluene:ethyl acetate=7:3) showed that the reaction was complete. Then the product mixture was extracted with 10% citric acid to remove dimethylaminopyridine (DMAP), washed with acetonitrile (3 ml, 4 times) to remove excess of p-nitrophenyl chloroformate. Pure product was dried in vacuo over $P_2O_5$. Yield: 557 mg(88%). %). $^1H$ NMR ($CHCl_3$, 360 MHz) δ 0.88 (t, end $CH_3$, 6H); 1.25 (s, 28×$CH_2$, 56H); 1.58 (m, $CH_2CH_2CO$, 4H); 2.34 (2×t, $CH_2CO$, 4H); 4.22 (trans d, $CH_2OCOC_{17}H_{35}$, 1H); 4.35 (m, $OCOOCH_2CH$, 2H); 4.51 (cis d, $CH2OCOC_{17}H_{35}$, 1H); 5.37 (m, $OCOOCH_2CH$, 1H); 7.39 (d, $C_6H_5$, 2H); 8.28 (d, $C_6H_5$, 2H).

Ethylene diamine (42 µl, 0.63 mmol, 5 fold excess), and pyridine (200 µl, were added in $CHCl_3$ (1 ml). 2-disteroyl-sn-p-nitrophenyl carbonate (100 mg, 0.13 mmol) was dissolved in $CHCl_3$ (1 ml) and added dropwise to ethylene diamine solution with a pasteur pipette at 0° C. (ice water) and continued overnight (16 h). TLC ($CHCl_3$:MeOH:$H_2O$ 90:18:2, and $CHCl_3$:MeOH=90:10) showed that the reaction was complete. Solvent was evaporated to remove pyridine. Then the product mixture was dissolved in $CHCl_3$, loaded onto the column (Aldrich, Silica gel, 60° A, 200–400 mesh), and eluted with $CHCl_3$:$CH_3COCH_3$, and $CHCl_3$:MeOH gradient, $CHCl_3$:$CH_3COCH_3$=90:10, 60 ml (upper spot eluted); $CHCl_3$:NeOH=90:10, 60 ml (product eluted). Fractions containing pure product were combined and evaporated. Tert-butanol was added and dried in vacuo over $P_2O_5$. Yield: 64 mg (75%). $^1H$ NMR (DMSO-$d_6$, 360 MHz) δ 0.83 (t, end $CH_3$, 6H); 1.22 (s, 28×$CH_2$, 56H); 1.51 (m, $CH_2CH_2CO$, 4H); 2.25 (2×t, $CH_2CO$, 4H); 2.83 (m, $H_2NCH_2CH_2NH$, 2H); 3.21 (m, $H_2NCH_2CH_2NH$, 2H); 4.10–4.14 (m & cis d, $COOCH_2CHCH_2$, 4H); 5.17 (m, $OCOOCH_2CH$, 1H); 7.78 (m, $H_2NCH_2CH_2NH$, 2H).

mPEG-MeDTB-nitrophenylchloroformate (400 mg, 0.162 mmol, 2.2 eq) was dissolved in $CHCl_3$ in (2 ml). 1,2-steroyl-sn-ethylene amine (51 mg, 0.075 mmol) and TEA (37 µl, 0.264 mmol, 3.52 eq) were added to the solution. Then the reaction mixture was stirred at 45° C. for 20 minutes. TLC ($CHCl_3$:MeOH:$H_2O$=90:18:2, and $CHCl_3$:MeOH=90:10) showed that the reaction went to completion. Solvent was evaporated. The product mixture was dissolved in methanol. 2 g of C8 silica was added and then solvent was evaporated. C8 silica containing product mixture was added on the top of the C8 column ((Supelco, Supel clean. Lot no. SP0824), and was eluted with MeOH:$H_2O$ gradient (pressure), MeOH:$H_2O$=60:40, 40 ml; MeOH:$H_2O$=70:30, 80 ml (starting material eluted); MeOH:$H_2O$=80:20, 40 ml; MeOH:$H_2O$=90:10=20 ml; $CHCl_3$:MeOH:$H_2O$=5:80:15, 20 mi; $CHCl_3$:MeOH:$H_2O$= 90:18:10, 40 ml (product eluted). Fractions containing pure product were combined and evaporated to give product as colorless thick liquid. Tertiary butanol (5 ml) was added and the solution was lyophilized and then dried in vacuo over $P_2O_5$ to give product as white solid (200 mg, 89% yield). $^1H$ NMR (DMSO-$d_6$, 360 MHz) δ δ 0.83 (t, end $CH_3$, 6H); 1.22 (s, 28×$CH_2$, 56H); 1.48 (m, $CH_2CH_2CO$, 4H); 2.25 (2×t, $CH_2CO$, 4H); 3.10 (m, $HNCH_2CH_2NH$, 4H); 3.50 (s, PEG, 180H); 4.04 (t, mPEG-$CH_2$, 2H); 4.09 (trans d, $COOCH_2CHCH_2$, 1H); 4.25 (cis d, $COOCH_2CHCH_2$, 1H); 4.98 (s, $C_6H_5CH_2OCO$, 2H); 5.23 (m, $COOCH_2CHCH_2$, 1H); 7.18 (m, $NHCH_2CH_2NH$, 2H); 7.33 (d, $C_6H_5$, 2H); 7.38 (m, mPEG-OCONH, 1H); 7.52 (d, $C_6H_5$, 2H).

Example 6

Preparation of Liposomes Containing Nucleic Acid

Liposomes were prepared by preparing a solution of the desired lipid components in an organic solvent in the desired molar ratio and then hydrated with 5% glucose, pH 4 to 5. The lipid components and the mole ratio of the components are specified in the Examples below.

A pNSL plasmid encoding for luciferase was constructed as described in U.S. Pat. No. 5,851,818 from two commercially available plasmids, pGFP-N1 plasmid (Clontech, Palo Alto, Calif.) and pGL3-C (Promega Corporation, Madison, Wis.). The luciferase reporter plasmid DNA solution was added to the acidic liposome solution slowly with continuous stirring for 10 minutes.

FGF or folate ligands were conjugated to maleimide-PEG-DSPE, according to procedures known in the art (Gabizon, A. et al, *Bioconjugate Chem.*, 10:289 (1999)). DNA-liposome complexes were incubated with micellar solutions of mPEG-DSPE, FGF-PEG-DSPE or folate-PEG-DSPE with continuous stirring for 20 minutes to achieve insertion of the ligand-PEG-lipid into the pre-formed liposomes.

Example 7

In vivo Transfection and Expression in Tumor Tissue

A. Tumor Models

KB tumor cells (1 million cells) were inoculated subcutaneously to the flank of nude mice. The mice were fed a reduced folate diet to upregulate the expression of folate receptors on the KB tumor cells. This model was used for folate-conjugated liposome-DNA complexes to target tumor vasculature angiogenic endothelial cells.

Lewis lung carcinoma cells (1 million cells) were inoculated subcutaneously to the flank of $B6C_3$-F1 mice. FGF receptors were expressed either on the surface of angiogenic endothelial cells or tumor cells. This model was used for FGF-conjugated liposome-DNA complexes to target tumor vasculature angiogenic endothelial cells.

B. Liposome Formulations

Five liposome formulations were prepared as described in Example 6 with the following lipid components:

| Component | Amount |
| --- | --- |
| Formulation No. 7-1 | |
| HDSG Neutral-cationic lipid (Compound V of FIG. 1) | 60 mole percent of total lipids |
| Cholesterol | 40 mole percent of total lipids |
| luciferase plasmid | 100 µg |
| FGF targeting ligand | 15 FGF/liposome |

| Component | Amount |
|---|---|
| Formulation No. 7-2 | |
| HDSG Neutral-cationic lipid (Compound V of FIG. 1) | 60 mole percent of total lipids |
| cholesterol | 40 mole percent of total lipids |
| mPEG-DTB-DSPE ("FC PEG") | 5 mole percent of total lipids |
| luciferase plasmid | 100 µg |
| FGF targeting ligand | 15 FGF/liposome |
| Formulation No. 7-3 | |
| HDSG Neutral-cationic lipid (Compound V of FIG. 1) | 40 mole percent of total lipids |
| PHSPC | 60 mole percent of total lipids |
| mPEG-DTB-DSPE ("FC PEG") | 5 mole percent of total lipids |
| luciferase plasmid | 100 µg |
| FGF targeting ligand | 15 FGF/liposome |
| Formulation No. 7-4 | |
| HDSG Neutral-cationic lipid (Compound V of FIG. 1) | 40 mole percent of total lipids |
| PHSPC | 60 mole percent of total lipids |
| mPEG-DSPE | 5 mole percent of total lipids |
| luciferase plasmid | 100 µg |
| FGF targeting ligand | 15 FGF/liposome |
| Formulation No. 7-5 | |
| DDAB | 55 mole percent of total lipids |
| PHSPC | 45 mole percent of total lipids |
| luciferase plasmid | 100 µg |
| folate targeting ligand | 15 FGF/liposome |

C. In vivo Administration

Fifteen test mice injected with Lewis lung carcinoma cells were randomly divided into four test groups to receive one of Formulations 1–5. The liposome-DNA complexes were administered intravenously at a dose of 200 µg DNA plasmid. Tumor and other tissues were collected 24 hours after treatment and luciferase expression was determined by luciferase assay from the tissue extracts. The results are shown in Table 1.

Example 8

In vivo Administration of FGF-Targeted Liposome-DNA Complexes

A. Matrigel Tumor Model

A Matrigel® model in mice was employed for tumor vasculature targeting of FGF-angiogenic endothelial cells. Angiogenic endothelial cells in Matrigel® are similar to vasculature angiogenic endothelial cells in tumor, these endothelial cells (endothelial cells only, without tumor cells) in Matrigel® were used to mimic endothelial cells in tumor for the study of in vivo FGF-targeted liposome/nucleic acid complex transfection and expression. Matrigel® forms a solid gel when injected into mice subcutaneously and induces a rapid and intense angiogenic reaction.

B. Liposome Formulations

Nine liposome formulations were prepared as described in Example 6 with the following lipid components:

| Component | Amount |
|---|---|
| Formulation No. 8-1 | |
| DOTAP | 55 mole percent of total lipids |
| cholesterol | 45 mole percent of total lipids |
| luciferase plasmid | 100 µg |
| Formulation No. 8-2 | |
| HDSG Neutral-cationic lipid (Compound V of FIG. 1) | 40 mole percent of total lipids |
| PHSPC | 60 mole percent of total lipids |
| luciferase plasmid | 200 µg |
| FGF targeting ligand | 15 FGF/liposome |
| Formulation No. 8-3 | |
| HDSG Neutral-cationic lipid (Compound V of FIG. 1) | 40 mole percent of total lipids |
| PHSPC | 60 mole percent of total lipids |
| FC-PEG | 1 mole percent of total lipids |
| luciferase plasmid | 200 µg |
| FGF targeting ligand | 15 FGF/liposome |
| Formulation No. 8-4 | |
| HDSG Neutral-cationic lipid (Compound V of FIG. 1) | 35 mole percent of total lipids |
| DOTAP | 30 mole percent of total lipids |
| PHSPC | 35 mole percent of total lipids |
| luciferase plasmid | 200 µg |
| Formulation No. 8-5 | |
| HDSG Neutral-cationic lipid (Compound V of FIG. 1) | 35 mole percent of total lipids |
| DOTAP | 30 mole percent of total lipids |
| PHSPC | 35 mole percent of total lipids |
| luciferase plasmid | 200 µg |
| FGF targeting ligand | 15 FGF/liposome |
| Formulation No. 8-6 | |
| HDSG Neutral-cationic lipid (Compound V of FIG. 1) | 35 mole percent of total lipids |
| DOTAP | 30 mole percent of total lipids |
| PHSPC | 35 mole percent of total lipids |
| FC-PEG | 1 mole percent of total lipids |
| luciferase plasmid | 200 µg |
| FGF targeting ligand | 15 FGF/liposome |
| Formulation No. 8-7 | |
| HDSG Neutral-cationic lipid (Compound V of FIG. 1) | 42.5 mole percent of total lipids |
| GC33 | 22.5 Mole percent of total lipids |
| PHSPC | 35 Mole percent of total lipids |
| luciferase plasmid | 250 µg |
| Formulation No. 8-8 | |
| HDSG Neutral-cationic lipid (Compound V of FIG. 1) | 42.5 mole percent of total lipids |

-continued

| Component | Amount |
|---|---|
| GC33 | 22.5 mole percent of total lipids |
| PHSPC | 35 mole percent of total lipids |
| luciferase plasmid | 250 µg |
| FGF targeting ligand | 15 FGF/liposome |
| Formulation No. 8-9 | |
| HDSG Neutral-cationic lipid (Compound V of FIG. 1) | 42.5 mole percent of total lipids |
| GC33 | 22.5 mole percent of total lipids |
| PHSPC | 35 mole percent of total lipids |
| FC-PEG | 1 mole percent of total lipids |
| luciferase plasmid | 250 µg |
| FGF targeting ligand | 15 FGF/liposome |

C. In vivo Administration

Twenty-seven mice were injected with Matrigel. Six days after implantation of the Matrigel, the mice were randomized into treatment groups (n=3) for treatment with one of nine formulations described in section B above. The liposome-DNA complexes were administered intravenously at a dose of 200 µg DNA plasmid. Twenty-four hours after administration of the FGF-targeted liposome-DNA complexes, luciferase expression in the matrigel, lung and liver was measured. The results are shown in Table 2.

Example 9

In vivo Administration of FGF-Targeted Liposome-DNA Complexes

A. Test Animals

Mice were inoculated with Lewis lung carcinoma cells as described in Example 7A.

B. Liposome Formulations

Nine liposome formulations were prepared as described in Example 6 with the following lipid components:

| Component | Amount |
|---|---|
| Formulation No. 9-1 | |
| DOTAP | 55 mole percent of total lipids |
| cholesterol | 45 mole percent of total lipids |
| luciferase plasmid | 100 µg |
| Formulation No. 9-2 | |
| HDSG Neutral-cationic lipid (Compound V of FIG. 1) | 40 mole percent of total lipids |
| PHSPC | 60 mole percent of total lipids |
| luciferase plasmid | 200 µg |
| FGF targeting ligand | 15 FGF/liposome |
| Formulation No. 9-3 | |
| HDSG Neutral-cationic lipid (Compound V of FIG. 1) | 40 mole percent of total lipids |
| PHSPC | 60 mole percent of total lipids |
| FC-PEG | 1 mole percent of total lipids |
| luciferase plasmid | 200 µg |
| FGF targeting ligand | 15 FGF/liposome |

-continued

| Component | Amount |
|---|---|
| Formulation No. 9-4 | |
| HDSG Neutral-cationic lipid (Compound V of FIG. 1) | 35 mole percent of total lipids |
| DOTAP | 30 mole percent of total lipids |
| PHSPC | 35 mole percent of total lipids |
| luciferase plasmid | 200 µg |
| Formulation No. 9-5 | |
| HDSG Neutral-cationic lipid (Compound V of FIG. 1) | 35 mole percent of total lipids |
| DOTAP | 30 mole percent of total lipids |
| PHSPC | 35 mole percent of total lipids |
| luciferase plasmid | 200 µg |
| FGF targeting ligand | 15 FGF/liposome |
| Formulation No. 9-6 | |
| HDSG Neutral-cationic lipid (Compound V of FIG. 1) | 35 mole percent of total lipids |
| DOTAP | 30 mole percent of total lipids |
| PHSPC | 35 mole percent of total lipids |
| FC-PEG | 1 mole percent of total lipids |
| luciferase plasmid | 200 µg |
| FGF targeting ligand | 15 FGF/liposome |
| Formulation No. 9-7 | |
| HDSG Neutral-cationic lipid (Compound V of FIG. 1) | 42.5 mole percent of total lipids |
| GC33 | 22.5 Mole percent of total lipids |
| PHSPC | 35 Mole percent of total lipids |
| luciferase plasmid | 250 µg |
| Formulation No. 9-8 | |
| HDSG Neutral-cationic lipid (Compound V of FIG. 1) | 42.5 mole percent of total lipids |
| GC33 | 22.5 mole percent of total lipids |
| PHSPC | 35 mole percent of total lipids |
| luciferase plasmid | 250 µg |
| FGF targeting ligand | 15 FGF/liposome |
| Formulation No. 9-9 | |
| HDSG Neutral-cationic lipid (Compound V of FIG. 1) | 42.5 mole percent of total lipids |
| GC33 | 22.5 mole percent of total lipids |
| PHSPC | 35 mole percent of total lipids |
| FC-PEG | 1 mole percent of total lipids |
| luciferase plasmid | 250 µg |
| FGF targeting ligand | 15 FGF/liposome |

C. In vivo Administration

Nine-days after inoculation with tumor cells, twenty-seven tumor-bearing mice were randomized into treatment groups (n=3) for treatment with one of nine formulations, Formulation No. (9-1) through Formulation No. (9-9). The liposome-DNA complexes were administered intravenously at a dose of 200 µg DNA plasmid. Twenty-four hours after administration of the FGF-targeted liposome-DNA complexes, luciferase expression in the tumor, lung and liver was measured. The results are shown in Table 3.

Example 10

In vivo Administration of FGF-Targeted Liposome-DNA Complexes

A. Test Animals

Mice were inoculated with Lewis lung carcinoma cells as described in Example 7A. On the opposing flank, Matrigel was injected as described in Example 8A.

B. Liposome Formulations

Seven liposome formulations were prepared as described in Example 6 with the following lipid components:

| Component | Amount |
|---|---|
| Formulation No. 10-1 | |
| DOTAP | 55 mole percent of total lipids |
| cholesterol | 45 mole percent of total lipids |
| luciferase plasmid | 100 μg |
| Formulation No. 10-2 | |
| HDSG Neutral-cationic lipid (Compound V of FIG. 1) | 35 mole percent of total lipids |
| DOTAP | 30 mole percent of total lipids |
| CHOL | 35 mole percent of total lipids |
| luciferase plasmid | 200 μg |
| Formulation No. 10-3 | |
| HDSG Neutral-cationic lipid (Compound V of FIG. 1) | 35 mole percent of total lipids |
| DOTAP | 30 mole percent of total lipids |
| CHOL | 35 mole percent of total lipids |
| luciferase plasmid | 200 μg |
| FGF targeting ligand | 15 FGF/liposome |
| Formulation No. 10-4 | |
| HDSG Neutral-cationic lipid (Compound V of FIG. 1) | 35 mole percent of total lipids |
| DOTAP | 30 mole percent of total lipids |
| CHOL | 35 mole percent of total lipids |
| FC-PEG | 1 mole percent of total lipids |
| luciferase plasmid | 200 μg |
| FGF targeting ligand | 15 FGF/liposome |
| Formulation No. 10-5 | |
| HDSG Neutral-cationic lipid (Compound V of FIG. 1) | 53.75 mole percent of total lipids |
| GC33 | 11.25 mole percent of total lipids |
| PHSPC | 35 mole percent of total lipids |
| luciferase plasmid | 200 μg |
| Formulation No. 10-6 | |
| HDSG Neutral-cationic lipid (Compound V of FIG. 1) | 53.75 mole percent of total lipids |
| GC33 | 11.25 mole percent of total lipids |
| PHSPC | 35 mole percent of total lipids |
| luciferase plasmid | 200 μg |
| FGF targeting ligand | 15 FGF/liposome |
| Formulation No. 10-7 | |
| HDSG Neutral-cationic lipid (Compound V of FIG. 1) | 53.75 mole percent of total lipids |
| GC33 | 11.25 mole percent of total lipids |
| PHSPC | 35 mole percent of total lipids |
| FC-PEG | 1 mole percent of total lipids |
| luciferase plasmid | 200 μg |
| FGF targeting ligand | 15 FGF/liposome |

C. In vivo Administration

Nine-days after inoculation with tumor cells, 21 tumor-bearing mice were randomized into treatment groups (n=3) for treatment with one of formulations, Formulation No. (10-1) through Formulation No. (10-7). The liposome-DNA complexes were administered intravenously at a dose of 200 μg DNA plasmid. Twenty-four hours after administration of the FGF-targeted liposome-DNA complexes, luciferase expression in the matrigel, tumor, lung and liver was measured. The results are shown in Table 4.

Example 11

In vivo Administration of FGF-Targeted Liposome-DNA Complexes

A. Test Animals

Mice were implanted with Matrigel as described in Example 8A.

B. Liposome Formulations

Eight liposome formulations were prepared as described in Example 6 with the following lipid components:

| Component | Amount |
|---|---|
| Formulation No. 11-1 | |
| DOTAP | 55 mole percent of total lipids |
| cholesterol | 45 mole percent of total lipids |
| luciferase plasmid | 100 μg |
| Formulation No. 11-2 | |
| HDSG Neutral-cationic lipid (Compound V of FIG. 1) | 40 mole percent of total lipids |
| PHSPC | 60 mole percent of total lipids |
| luciferase plasmid | 200 μg |
| FGF targeting ligand | 15 FGF/liposome |
| Formulation No. 11-3 | |
| HDSG Neutral-cationic lipid (Compound V of FIG. 1) | 35 mole percent of total lipids |
| DOTAP | 30 mole percent of total lipids |
| PHSPC | 35 mole percent of total lipids |
| luciferase plasmid | 200 μg |
| FGF targeting ligand | 15 FGF/liposome |
| Formulation No. 11-4 | |
| HDSG Neutral-cationic lipid (Compound V of FIG. 1) | 35 mole percent of total lipids |
| DOTAP | 30 mole percent of total lipids |
| CHOL | 35 mole percent of total lipids |
| luciferase plasmid | 200 μg |
| Formulation No. 11-5 | |
| HDSG Neutral-cationic lipid (Compound V of FIG. 1) | 35 mole percent of total lipids |
| DOTAP | 30 mole percent of total lipids |
| CHOL | 35 mole percent of total lipids |
| luciferase plasmid | 200 μg |
| FGF targeting ligand | 15 FGF/liposome |
| Formulation No. 11-6 | |
| HDSG Neutral-cationic lipid (Compound V of FIG. 1) | 35 mole percent of total lipids |
| DOTAP | 30 mole percent of total lipids |
| CHOL | 35 mole percent of total lipids |
| FC-PEG | 4 mole percent of total lipids |
| luciferase plasmid | 200 μg |
| FGF targeting ligand | 15 FGF/liposome |
| Formulation No. 11-7 | |
| HDSG Neutral-cationic lipid (Compound V of FIG. 1) | 35 mole percent of total lipids |
| DOTAP | 30 mole percent of total lipids |
| CHOL | 35 mole percent of total lipids |
| luciferase plasmid | 200 μg |
| sialyl-Lewis X targeting ligand | 15 /liposome |
| Formulation No. 11-8 | |
| HDSG Neutral-cationic lipid (Compound V of FIG. 1) | 45 mole percent of total lipids |
| DOTAP | 20 mole percent of total lipids |
| CHOL | 35 mole percent of total lipids |
| luciferase plasmid | 200 μg |
| FGF targeting ligand | 15 FGF/liposome |

C. In vivo Administration

Six-days after implantation of Matrigel, 24 mice were randomized into treatment groups (n=3) for treatment with one of the formulations, Formulation No. (11-1) through Formulation No. (11-8). The liposome-DNA complexes were administered intravenously at a dose of 200 μg DNA plasmid. Twenty-four hours after administration of the FGF-targeted liposome-DNA complexes, luciferase expression in the matrigel, lung and liver was measured. The results are shown in Table 5.

Example 12

In vivo Administration of FGF-Targeted Liposome-DNA Complexes

A. Test Animals

Mice were inoculated with Lewis lung carcinoma cells as described in Example 7A.

B. Liposome Formulations

Five liposome formulations were prepared as described in Example 6 with the following lipid components:

| Component | Amount |
|---|---|
| Formulation No. 12-1 | |
| DOTAP | 55 mole percent of total lipids |
| cholesterol | 45 mole percent of total lipids |
| luciferase plasmid | 100 µg |
| Formulation No. 12-2 | |
| Component (>5 days) | |
| HDSG Neutral-cationic lipid (Compound V of FIG. 1) | 40 mole percent of total lipids |
| PHSPC | 60 mole percent of total lipids |
| luciferase plasmid | 200 µg |
| FGF targeting ligand | 15 FGF/liposome |
| Formulation No. 12-3 | |
| Component (1 day) | |
| HDSG Neutral-cationic lipid (Compound V of FIG. 1) | 40 mole percent of total lipids |
| PHSPC | 60 mole percent of total lipids |
| luciferase plasmid | 200 µg |
| FGF targeting ligand | 15 FGF/liposome |
| Formulation No. 12-4 | |
| Component (>5 days) | |
| HDSG Neutral-cationic lipid (Compound V of FIG. 1) | 35 mole percent of total lipids |
| DOTAP | 30 mole percent of total lipids |
| cholesterol | 35 mole percent of total lipids |
| FC-PEG | 1 mole percent of total lipids |
| luciferase plasmid | 200 µg |
| FGF targeting ligand | 15 FGF/liposome |
| Formulation No. 12-5 | |
| Component (1 day) | |
| HDSG Neutral-cationic lipid (Compound V of FIG. 1) | 35 mole percent of total lipids |
| DOTAP | 30 mole percent of total lipids |
| cholesterol | 35 mole percent of total lipids |
| FC-PEG | 1 mole percent of total lipids |
| luciferase plasmid | 200 µg |
| FGF targeting ligand | 15 FGF/liposome |

C. In vivo Administration

Nine-days after inoculation with tumor cells, 15 tumor-bearing mice were randomized into treatment groups (n=3) for treatment with one of nine formulations, Formulation No. (12-1) through Formulation No. (12-5). The liposome-DNA complexes were administered intravenously at a dose of 100 µg DNA plasmid. Twenty-four hours after administration of Formulation Nos. 12-1, 12-3 and 12-5, and five days after administration of Formulation Nos. 12-2 and 12-4, luciferase expression in the tumor, lung and liver was measured. The results are shown in Table 6, where expression was measured 24 hours after liposome administration of Formulation Nos. 12-1, 12-3 and 12-5, and five days after administration of Formulation Nos. 12-2 and 12-4.

Example 13

In vivo Administration of Folate-Targeted Liposome-DNA Complexes

A. Test Animals

Mice were inoculated with KB carcinoma cells and cared for as described in Example 7A.

B. Liposome Formulations

Eight liposome formulations were prepared as described in Example 6 with the following lipid components:

| Component | Amount |
|---|---|
| Formulation No. 13-1 | |
| DOTAP | 55 mole percent of total lipids |
| cholesterol | 45 mole percent of total lipids |
| luciferase plasmid | 100 µg |
| Formulation No. 13-2 | |
| HDSG Neutral-cationic lipid (Compound V of FIG. 1) | 40 mole percent of total lipids |
| PHSPC | 60 mole percent of total lipids |
| luciferase plasmid | 200 µg |
| folate targeting ligand | 30 folate/liposome |
| Formulation No. 13-3 | |
| HDSG Neutral-cationic lipid (Compound V of FIG. 1) | 40 mole percent of total lipids |
| PHSPC | 60 mole percent of total lipids |
| FC-PEG | 4 mole percent of total lipids |
| luciferase plasmid | 200 µg |
| folate targeting ligand | 30 folate/liposome |
| Formulation No. 13-4 | |
| HDSG Neutral-cationic lipid (Compound V of FIG. 1) | 35 mole percent of total lipids |
| DOTAP | 30 mole percent of total lipids |
| PHSPC | 35 mole percent of total lipids |
| luciferase plasmid | 200 µg |
| folate targeting ligand | 30 folate/liposome |
| Formulation No. 13-5 | |
| HDSG Neutral-cationic lipid (Compound V of FIG. 1) | 35 mole percent of total lipids |
| DOTAP | 30 mole percent of total lipids |
| PHSPC | 35 mole percent of total lipids |
| FC-PEG | 4 mole percent of total lipids |
| luciferase plasmid | 200 µg |
| folate targeting ligand | 30 folate/liposome |
| Formulation No. 13-6 | |
| HDSG Neutral-cationic lipid (Compound V of FIG. 1) | 42.5 mole percent of total lipids |
| GC33 | 22.5 mole percent of total lipids |
| PHSPC | 35 mole percent of total lipids |
| luciferase plasmid | 250 µg |
| folate targeting ligand | 30 folate/liposome |
| Formulation No. 13-7 | |
| HDSG Neutral-cationic lipid (Compound V of FIG. 1) | 42.5 mole percent of total lipids |
| GC33 | 22.5 mole percent of total lipids |
| PHSPC | 35 mole percent of total lipids |
| FC-PEG | 4 mole percent of total lipids |
| luciferase plasmid | 250 µg |
| folate targeting ligand | 30 folate/liposome |
| Formulation No. 13-8 | |
| HDSG Neutral-cationic lipid (Compound V of FIG. 1) | 42.5 mole percent of total lipids |
| GC33 | 22.5 mole percent of total lipids |
| PHSPC | 35 mole percent of total lipids |
| FC-PEG | 4 mole percent of total lipids |

-continued

| Component | Amount |
| --- | --- |
| luciferase plasmid | 250 µg |
| folate targeting ligand | 30 folate/liposome |

C. In vivo Administration

Nine-days after inoculation with tumor cells, 24 tumor-bearing mice were randomized into treatment groups (n=3) for treatment with one of Formulation No. (13-1) through Formulation No. (13-8). The liposome-DNA complexes were administered intravenously at a dose of 100 µg DNA plasmid. Twenty-four hours after administration luciferase expression in the tumor, lung and liver was measured. The results are shown in Table 7.

Example 14

In vivo Administration of Folate-Targeted Liposome-DNA Complexes

A. Test Animals

Mice were inoculated with KB carcinoma cells and cared for as described in Example 7A.

B. Liposome Formulations

Six liposome formulations were prepared as described in Example 6 with the following lipid components:

| Component | Amount |
| --- | --- |
| Formulation No. 14-1 | |
| DOTAP | 55 mole percent of total lipids |
| cholesterol | 45 mole percent of total lipids |
| luciferase plasmid | 100 µg |
| Formulation No. 14-2 | |
| HDSG Neutral-cationic lipid (Compound V of FIG. 1) | 35 mole percent of total lipids |
| DOTAP | 30 mole percent of total lipids |
| cholesterol | 35 mole percent of total lipids |
| luciferase plasmid | 200 µg |
| folate targeting ligand | 30 folate/liposome |
| Formulation No. 14-3 | |
| HDSG Neutral-cationic lipid (Compound V of FIG. 1) | 35 mole percent of total lipids |
| DOTAP | 30 mole percent of total lipids |
| cholesterol | 35 mole percent of total lipids |
| FC-PEG | 4 mole percent of total lipids |
| luciferase plasmid | 200 µg |
| folate targeting ligand | 30 folate/liposome |
| Formulation No. 14-4 | |
| HDSG Neutral-cationic lipid (Compound V of FIG. 1) | 45 mole percent of total lipids |
| DOTAP | 20 mole percent of total lipids |
| cholesterol | 35 mole percent of total lipids |
| luciferase plasmid | 200 µg |
| folate targeting ligand | 30 folate/liposome |
| Formulation No. 14-5 | |
| HDSG Neutral-cationic lipid (Compound V of FIG. 1) | 45 mole percent of total lipids |
| DOTAP | 20 mole percent of total lipids |
| cholesterol | 35 mole percent of total lipids |
| FC-PEG | 4 mole percent of total lipids |
| luciferase plasmid | 200 µg |
| folate targeting ligand | 30 folate/liposome |

C. In vivo Administration

Nine-days after inoculation with tumor cells, 18 tumor-bearing mice were randomized into treatment groups (n=3) for treatment with one of Formulation No. (14-1) through Formulation No. (14-6). The liposome-DNA complexes were administered intravenously at a dose of 100 µg DNA plasmid. Twenty-four hours after administration luciferase expression in the tumor, lung and liver was measured. The results are shown in Table 8.

Example 15

In vivo Administration of Folate-Targeted Liposome-DNA Complexes

A. Test Animals

Mice were inoculated with KB carcinoma cells and cared for as described in Example 7A.

B. Liposome Formulations

Seven liposome formulations were prepared as described in Example 6 with the following lipid components:

| Component | Amount |
| --- | --- |
| Formulation No. 15-1 | |
| DOTAP | 55 mole percent of total lipids |
| cholesterol | 45 mole percent of total lipids |
| luciferase plasmid | 100 µg |
| Formulation No. 15-2 | |
| HDSG Neutral-cationic lipid (Compound V of FIG. 1) | 40 mole percent of total lipids |
| PHSPC | 60 mole percent of total lipids |
| luciferase plasmid | 200 µg |
| folate targeting ligand | 30 folate/liposome |
| Formulation No. 15-3 | |
| HDSG Neutral-cationic lipid (Compound V of FIG. 1) | 40 mole percent of total lipids |
| PHSPC | 60 mole percent of total lipids |
| FC-PEG | 4 mole percent of total lipids |
| luciferase plasmid | 200 µg |
| folate targeting ligand | 30 folate/liposome |
| Formulation No. 15-4 | |
| HDSG Neutral-cationic lipid (Compound V of FIG. 1) | 35 mole percent of total lipids |
| DOTAP | 30 mole percent of total lipids |
| PHSPC | 35 mole percent of total lipids |
| luciferase plasmid | 200 µg |
| folate targeting ligand | 30 folate/liposome |
| Formulation No. 15-5 | |
| HDSG Neutral-cationic lipid (Compound V of FIG. 1) | 35 mole percent of total lipids |
| DOTAP | 30 mole percent of total lipids |
| PHSPC | 35 mole percent of total lipids |
| FC-PEG | 2.3 mole percent of total lipids |
| luciferase plasmid | 200 µg |
| folate targeting ligand | 30 folate/liposome |
| Formulation No. 15-6 | |
| HDSG Neutral-cationic lipid (Compound V of FIG. 1) | 35 mole percent of total lipids |
| DOTAP | 30 mole percent of total lipids |
| cholesterol | 35 mole percent of total lipids |
| luciferase plasmid | 200 µg |
| folate targeting ligand | 30 folate/liposome |
| Formulation No. 15-7 | |
| HDSG Neutral-cationic lipid (Compound V of FIG. 1) | 35 mole percent of total lipids |

-continued

| Component | Amount |
| --- | --- |
| DOTAP | 30 mole percent of total lipids |
| cholesterol | 35 mole percent of total lipids |
| FC-PEG | 2.3 mole percent of total lipids |
| luciferase plasmid | 200 µg |
| folate targeting ligand | 30 folate/liposome |

C. In vivo Administration

Nine-days after inoculation with tumor cells, 21 tumor-bearing mice were randomized into treatment groups (n=3) for treatment with one of Formulation No. (15-1) through Formulation No. (15-7). The liposome-DNA complexes were administered intravenously at a dose of 100 µg DNA plasmid. Twenty-four hours after administration luciferase expression in the tumor, lung and liver was measured. The results are shown in Table 9.

Although the invention has been described with respect to particular embodiments, it will be apparent to those skilled in the art that various changes and modifications can be made without departing from the invention.

It is claimed:

1. A composition for administration of a nucleic acid, comprising:

(a) liposomes comprised of
(i) a lipid having the formula

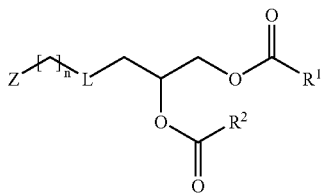

where each of $R^1$ and $R^2$ is an alkyl or alkenyl chain having between 8–24 carbon atoms, and each of $R^1$ or $R^2$ are independently selected;

n=0–20;

L is selected from the group consisting of (1) —X—(C=O)—Y—[[CH$_2$—]], (2) —X—(C=O)—, and (3) —X—[[CH$_2$—]], where X and Y are independently selected from oxygen, NH and a direct bond;

Z is a weakly basic moiety that has a pk of less than 7.4 and greater than about 4.0; and (ii) a compound having the general structure:

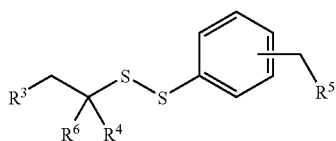

wherein $R^3$ is a hydrophilic polymer comprising a linkage for attachment to the dithiobenzyl moiety; $R^4$ is selected from the group consisting of H, alkyl and aryl; $R^5$ is selected from the group consisting of O(C=O)$R^7$, S(C=O)$R^7$, and O(C=S)$R^7$; $R^7$ comprises an amine-containing lipid; and $R^6$ is selected from the group consisting of H, alkyl and aryl; and where orientation of CH$_2$—$R^5$ is selected from the ortho position and the para position; and (b) a nucleic acid associated with said liposomes.

2. The composition of claim 1, wherein X is NH and Y is oxygen.

3. The composition of claim 1, wherein L is a carbamate linkage, an ester linkage, or a carbonate linkage.

4. The composition of claim 1, wherein L is NH—(C=O)—O—[[CH$_2$]].

5. The composition of claim 1, wherein Z is an imidazole.

6. The composition of claim 1, comprising between 1–80 mole percent of the lipid.

7. The composition of claim 1, wherein Z is a moiety having a pK value between 5.0–6.5.

8. The composition of claim 1, wherein each of $R^1$ and $R^2$ is an unbranched alkyl or alkenyl chain having between 8–24 carbon atoms.

9. The composition of claim 8, wherein each of $R^1$ and $R^2$ is $C_{17}H_{35}$.

10. The composition of claim 1, wherein n is between 1–10.

11. The composition of claim 1, wherein $R^6$ is H and $R^4$ is selected from the group consisting of CH$_3$, C$_2$H$_5$ and C$_3$H$_8$.

12. The composition of claim 1, wherein the amine-containing lipid comprises either a single hydrocarbon tail or a double hydrocarbon tail.

13. The composition of claim 1, wherein the amine-containing lipid is a phospholipid having a double hydrocarbon tail.

14. The composition of claim 1, wherein $R^4$ and $R^6$ are alkyls.

15. The composition of claim 1, wherein $R^3$ is selected from the group consisting of polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers thereof, and polyethyleneoxide-polypropylene oxide.

16. The composition of claim 1, wherein $R^3$ is polyethyleneglycol.

17. The composition of claim 16, wherein $R^6$ is H and $R^4$ is CH$_3$ or C$_2$H$_5$.

18. The composition of claim 1, wherein said liposomes include between 5–20 mole percent of the compound.

19. The composition of claim 1, further including a therapeutic compound entrapped in the liposomes.

20. The composition of claim 1, wherein said nucleic acid is entrapped in at least a portion of said liposomes.

21. The composition of claim 20, wherein the nucleic acid is selected from DNA, RNA, fragments thereof and oligonucleotides.

22. The composition of claim 1, further including a ligand for targeting the liposomes to a target site, said ligand covalently attached to a distal end of the hydrophilic polymer $R^3$ on said compound.

23. The composition of claim 22, wherein the ligand has binding affinity for endothelial tumor cells for internalization by such cells.

24. The composition of claim 22, wherein the ligand is selected from the group consisting of E-selectin, Her-2 and FGF.

25. The composition of claim 22, wherein said ligand is selected from the group consisting of c-erbB-2 protein product of the HER2/neu oncogene, epidermal growth factor (EGF) receptor, basic fibroblast growth receptor (basic FGF) receptor, vascular endothelial growth factor receptor, E-selectin receptor, L-selectin receptor, P-selectin receptor, folate receptor, CD4 receptor, CD19 receptor, $\alpha\beta$ integrin receptors, and chemokine receptors.

26. The composition of claim 1, wherein said liposomes further comprise a cationic lipid.

* * * * *